(12) United States Patent
Bagnoli et al.

(10) Patent No.: US 10,328,140 B2
(45) Date of Patent: Jun. 25, 2019

(54) MUTANT STAPHYLOCOCCAL ANTIGENS

(71) Applicant: GLAXOSMITHKLINE BIOLOGICALS SA, Rixensart (BE)

(72) Inventors: Fabio Bagnoli, Siena (IT); Luigi Fiaschi, Siena (IT); Maria Scarselli, Siena (IT)

(73) Assignee: GLAXOSMITHKLINE BIOLOGICALS S.A. (BE)

( * ) Notice: Subject to any disclaimer, the term of this patent is extended or adjusted under 35 U.S.C. 154(b) by 31 days.

(21) Appl. No.: 15/127,537

(22) PCT Filed: Mar. 24, 2015

(86) PCT No.: PCT/EP2015/056175
§ 371 (c)(1),
(2) Date: Sep. 20, 2016

(87) PCT Pub. No.: WO2015/144653
PCT Pub. Date: Oct. 1, 2015

(65) Prior Publication Data
US 2017/0143816 A1 May 25, 2017
US 2018/0064800 A9 Mar. 8, 2018

(30) Foreign Application Priority Data

Mar. 26, 2014 (EP) .................................... 14161861
Nov. 12, 2014 (EP) .................................... 14192913

(51) Int. Cl.
*A61K 39/085* (2006.01)
*A61K 39/00* (2006.01)
*A61K 49/00* (2006.01)
*C07K 14/31* (2006.01)

(52) U.S. Cl.
CPC ............ *A61K 39/085* (2013.01); *C07K 14/31* (2013.01); *A61K 2039/55511* (2013.01); *A61K 2039/645* (2013.01); *A61K 2039/70* (2013.01); *C07K 2319/00* (2013.01); *C07K 2319/40* (2013.01)

(58) Field of Classification Search
CPC ............................. A61K 39/00; A61K 39/085
USPC ...... 424/9.1, 9.2, 184.1, 185.1, 234.1, 243.1
See application file for complete search history.

(56) References Cited

FOREIGN PATENT DOCUMENTS

| WO | 2007/071692 A2 | 6/2007 |
|---|---|---|
| WO | 2007/145689 A1 | 12/2007 |
| WO | 2009/029831 A1 | 3/2009 |
| WO | 2010/119343 A2 | 10/2010 |
| WO | 2011/005341 A2 | 1/2011 |
| WO | 2011/127032 A1 | 10/2011 |
| WO | 2012/034067 A1 | 3/2012 |
| WO | 2013/030378 A1 | 3/2013 |

OTHER PUBLICATIONS

Dictionary of Microbiology and Molecular Biology, 2nd edition, Singleton & Sainsbury, eds., John Wiley & Sons Toronto, 1987, p. 452.*
Database WPI Week 201437, Thomson Scientific, London, GB; AN 2014-J07484, XP002739612, -& CN 103 645 318 A (Chongqing Yuanlun Biological Technology) Mar. 19, 2014 Abstract Sequence 1.
Database WPI Week 201440, Thomson Scientific, London, GB; AN 2014-K04482, XP002739613, -& CN 103 694 322 A (Chongqing Yuanlun Biological Technology) Apr. 2, 2014 Abstract, Sequences 1-4; Paragraphs [0268], [0270], [0299].
Fowler, et al., Effect of an Investigational Vaccine for Preventing *Staphylococcus aureus* Infections After Cardiothoracic Surgery, (2013) JAMA 309(13):1368-1378.
Kim, et al., Nontoxigenic protein A vaccine for methicillin-resistant *Staphylococcus aureus* infections in mice, (2010) J Exp Med 207(9):1863-1870.
Kuklin et al., A Novel *Staphylococcus aureus* Vaccine: Iron Surface Determinant B Induces Rapid Antibody Responses in Rhesus Macaques and Specific Increased Survival in a Murine *S. aureus* Sepsis Model, (2006) Infect Immun. 74(4):2215-2223.
Sjodahl, Repetitive Sequences in Protein A from *Staphylococcus aureus*—Arrangement of Five Regions within the Protein, Four being Highly Homologous and Fc-Binding, (1977) European J. Biochem. 73:343-351.
Uhlen et al., Complete sequence of the staphylococcal gene encoding protein A, (1984) J. Biol. Chem. 259: 13628.
Uhlen et al., Complete Sequence of the Staphylococcal Gene Encoding Protein A, (1984) J. Biol. Chem. 259 (3):1695-1702.
Wardenburg et al., Surface Proteins and Exotoxins are Required for the Pathogenesis of *Staphylococcus aureus* Pneumonia, (2007) Infect Immun 75(2):1040-1044.
International Search Report for Priority Application PCT/EP2015/056175.
Written Opinion for Priority Application PCT/EP2015/056175.

* cited by examiner

*Primary Examiner* — Rodney P Swartz

(57) ABSTRACT

Mutant protein A of *Staphylococcus aureus* (SpA) with decreased affinity for the Fcγ portion of human IgG is provided.

22 Claims, No Drawings
Specification includes a Sequence Listing.

MUTANT STAPHYLOCOCCAL ANTIGENS

This application is filed pursuant to 35 U.S.C. § 371 as a United States National Phase Application of International Patent Application Serial No. PCT/EP2015/056175 filed Mar. 24, 2015, which claims priority to European Application No. 14161861.1 filed Mar. 26, 2014, and to European Application No. 14192913.3 filed Nov. 12, 2014, and the entire contents of each of the foregoing applications are hereby incorporated by reference.

TECHNICAL FIELD

This invention relates to immunisation against infection by S. aureus.

BACKGROUND ART

*Staphylococcus aureus* is a Gram-positive spherical bacterium. Annual US mortality exceeds that of any other infectious disease, including HIV/AIDS, and *S. aureus* is the leading cause of bloodstream, lower respiratory tract, skin & soft tissue infections. It is also the predominant cause of bone infections worldwide, and these infections are painful, debilitating and difficult to treat.

Treatment of *S. aureus* is becoming increasingly challenging due to the development of antibiotic resistance by many strains of *S. aureus*. Methicillin-resistant *S. aureus* (MRSA) is found in over half of all community and hospital infections. Recent years have seen the emergence of MRSA strains which are also resistant to vancomycin, the antibiotic of last resort, and which are essentially untreatable.

There is currently no authorised vaccine. A vaccine based on a mixture of surface polysaccharides from bacterial types 5 and 8, StaphVAX™, failed to reduce infections when compared to the placebo group in a phase III clinical trial. Similarly, the V710 vaccine [1], based on the IsdB antigen [2], failed to reduce the rate of post-operative *S. aureus* infections [3].

The need for a vaccine is particularly acute due to problem of antibiotic resistance and the fact that *S. aureus* infection does not provide immunity from future infection thanks to its well-developed immune evasion capabilities. The immune evasion properties of *S. aureus* in turn render the development of effective vaccines more difficult. The mechanisms of immune evasion are not fully understood, but are at least in part due to staphylococcal protein A (SpA), an *S. aureus* surface molecule that binds to Fc of immunoglobulin (Ig) and to the Fab portion of VH3-type B cell receptors. Interaction of SpA with B cell receptors leads to clonal expansion and subsequent cell death of B cell populations, leading to ablation of the adaptive immune response. SpA binding to Ig Fc interferes with opsonophagocytic clearance of staphylococci by polymorphonuclear leukocytes.

Mutant forms of SpA with reduced affinity to immunoglobulins have been developed. WO2011/005341 describes a SpA with point mutations in each of the five Ig-binding domains which reduce the ability of the protein to bind to IgG.

Reference 4 discloses various approaches to providing improved *S. aureus* vaccines, including two preferred immunogen combinations referred to as "Combo-1" and "Combo-2". "Combo-1" included five antigens EsxA, EsxB, a mutant Hla, FhuD2, and Sta011, whereas "Combo-2" used a fragment of IsdA in place of the mutant Hla. Both of these combinations were tested with aluminium hydroxide adjuvants and they increased median survival time in a mouse model of infection when compared to buffer alone or to the IsdB antigen. "Combo-1" has also been tested with an aluminium hydroxide adjuvant and a TLR7 agonist, and the addition of the TLR7 agonist improved responses [5].

Despite the positive results with "Combo-1" and "Combo-2", there remains a need for further and improved compositions for immunising against *S. aureus*.

DISCLOSURE OF THE INVENTION

Protein A (SpA) (SEQ ID NO: 43), a cell wall anchored surface protein of *Staphylococcus aureus*, provides for bacterial evasion from innate and adaptive immune responses. Protein A binds immunoglobulins at their Fc portion, interacts with the VH3 domain of B cell receptors inappropriately stimulating B cell proliferation and apotosis, binds to von Willebrand factor A1 domains to activate intracellular clotting, and also binds to the TNF Receptor-1 to contribute to the pathogenesis of staphylococcal pneumonia. Due to the fact that Protein A captures immunoglobulin and displays toxic attributes, the possibility that this surface molecule may function as a vaccine in humans has not been rigorously pursued. Here the inventors demonstrate that Protein A variants no longer able to bind to immunoglobulins, which are thereby removed of their toxigenic potential, i.e, are non-toxigenic, stimulate humoral immune responses that protect against staphylococcal disease.

The invention therefore provides mutant SpA antigens as described below. Said mutants preferably have decreased affinity for the Fcγ portion of human IgG relative to unmodified SpA. The mutants may also have decreased affinity, relative to unmodified SpA, for the Fab portion of $V_H3$-containing human B cell receptors.

The inventors have found that the known "Combo-1" vaccine can be improved by adding a mutant staphylococcal protein A (SpA) which has been modified to decrease its affinity for the Fcγ portion of human IgG and for the Fab portion of $V_H3$-containing B cell receptors. This extra antigen increases the combination's protective efficacy and provides striking results in a renal abscess model. None of the antigen combinations tested in reference 4 included a SpA antigen.

The invention therefore further provides an immunogenic composition comprising EsxA, EsxB, FhuD2, Sta011, and Hla antigens, characterised in that the composition additionally includes a mutant SpA antigen, wherein the mutant has decreased affinity, relative to unmodified SpA, for the Fcγ portion of human IgG and for the Fab portion of $V_H3$-containing human B cell receptors.

The invention also provides an immunogenic composition comprising: (i) at least one antigen selected from the group consisting of EsxA, EsxB, FhuD2, Sta011, and Hla antigens; and (ii) a mutant SpA antigen which has decreased affinity, relative to unmodified SpA, for the Fcγ portion of human IgG and for the Fab portion of $V_H3$-containing human B cell receptors. Thus 1, 2, 3, 4 or preferably all 5 of EsxA, EsxB, FhuD2, Sta011, and Hla can be used in combination with the mutant SpA.

Unless defined otherwise, all technical and scientific terms used herein have the same meaning as commonly understood to one skilled in the relevant art.

For convenience, the meaning of certain terms and phrases employed in the specification, examples and claims are provided.

S. aureus Antigens

The invention relates inter alia to a mutant SpA antigen. The wild-type SpA (staphylococcal protein A) is a cell wall-anchored surface protein which is a crucial virulence factor for lung infections, septicemia, and abscess development and is expressed by most clinical *S. aureus* isolates. Wild-type SpA binds to the Fc portion of human IgG, to $V_H3$-containing B cell receptors, to von Willebrand factor at its A1 domain, and to the TNF-α receptor 1. Interaction of SpA with B cell receptors leads to clonal expansion and subsequent cell death of B cell populations with effects on adaptive and innate immune responses, whereas its binding to the Fcγ of IgG interferes with opsonophagocytic clearance of staphylococci by polymorphonuclear leukocytes. The N-terminal part of mature SpA is comprised of four or five 56-61-residue Ig-binding domains, which fold into triple helical bundles connected by short linkers, and are designated in order E, D, A, B, and C [6]. These domains display ~80% identity at the amino acid level, are 56 to 61 residues in length, and are organized as tandem repeats [7]. The C-terminal region is comprised of "Xr", a highly repetitive yet variable octapeptide, and "Xc", a domain which abuts the cell wall anchor structure of SpA.

In the NCTC 8325 strain spa is SAOUHSC_00069 and has amino acid sequence SEQ ID NO: 43 (GI:88193885). In the Newman strain it is nwmn_0055 (GI:151220267). SpA antigens used with the invention can elicit an antibody (e.g. when administered to a human) that recognises SEQ ID NO: 43 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 43; and/or (b) comprising a fragment of at least 'n' consecutive amino acids of SEQ ID NO: 43, wherein 'n' is 7 or more (e.g. 8, 10, 12, 14, 16, 18, 20, 25, 30, 35, 40, 50, 60, 70, 80, 90, 100, 150, 200, 250 or more). These SpA antigens include variants of SEQ ID NO: 43. Preferred fragments of (b) comprise an epitope from SEQ ID NO: 43. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 43 while retaining at least one epitope of SEQ ID NO: 43. The final 35 C-terminal amino acids of SEQ ID NO: 43 can usefully be omitted. The first 36 N-terminal amino acids of SEQ ID NO: 43 can usefully be omitted. Reference 8 suggests that individual IgG-binding domains might be useful immunogens, alone or in combination.

A useful fragment of SEQ ID NO: 43 is amino acids 37 to 325. This fragment contains all the five SpA Ig-binding domains (which are naturally arranged from N- to C-terminus in the order E, D, A, B, C) and includes the most exposed domain of SpA. It also reduces the antigen's similarity with human proteins. Other useful fragments may omit 1, 2, 3 or 4 of the natural A, B, C, D and/or E domains to prevent the excessive B cell expansion and then apoptosis which might occur if spa functions as a B cell superantigen. As reported in reference 18, other useful fragments may include only 1, 2, 3 or 4 of the natural A, B, C, D and/or E domains e.g. comprise only the SpA(A) domain but not B to E, or comprise only the SpA(D) domain but not A, B, C or E, etc. Thus a spa antigen useful with the invention may include 1, 2, 3, 4 or 5 IgG-binding domains, but ideally has 4 or fewer.

Thus, another useful fragment of SpA comprises or consists of the amino acid sequence of SEQ ID NO: 50 wherein the amino acid doublet at positions 60 and 61 is not Gln-Gln. Said doublet may be mutated as described below, for example to Lys-Arg. Thus, said fragment may comprise or consist of SEQ ID NO: 51 or 52.

If an antigen includes only one type of spa domain (e.g. only the Spa(A), SpA(D) or Spa(E) domain), it may include more than one copy of this domain e.g. multiple SpA(E) domains in a single polypeptide chain. It may also include one type of SpA domain and another protein or polypeptide. Thus, an antigen of the invention may be a fusion protein comprising only one type of SpA domain, such as the SpA(E) domain, and another protein antigen, such as EsxA; EsxB; FhuD2; Sta011; and Hla.

SpA antigens of the invention are mutated relative to SEQ ID NO: 43, such that they have decreased affinity for the Fcγ portion of human IgG. For instance, the QQ dipeptide at residues 60-61 of SEQ ID NO: 43 can be mutated to reduce affinity for immunoglobulins. Useful dipeptide substitutions for a QQ dipeptide are discussed below, and a preferred substitution is KR dipeptide. Thus a useful SpA antigen can comprise SEQ ID NO: 49, in which one or more (preferably all) of the 11 XX dipeptides differ from the corresponding dipeptides within SEQ ID NO: 43. For instance, the SpA antigen can comprise SEQ ID NO: 46, and a preferred example of SEQ ID NO: 46 is SEQ ID NO: 47. When expressed with a N-terminal methionine, the SpA antigen comprising SEQ ID NO: 47 can consist of SEQ ID NO: 48.

SpA antigens used with the invention may be further mutated relative to SEQ ID NO: 43, such that they have decreased affinity for the Fcγ portion of human IgG and for the Fab portion of $V_H3$-containing human B cell receptors. This can be achieved and assessed by, for instance, following the guidance in reference 9. Thus at least one Gln-Gln dipeptide in wild-type SpA can be mutated (e.g. to Lys-Lys; other possible mutations include Arg-Arg, Arg-Lys, Lys-Arg, Ala-Ala, Ser-Ser, Ser-Thr, Thr-Thr, etc.) and/or at least one Asp-Asp dipeptide in wild-type SpA can be mutated (e.g. to Ala-Ala; other possible mutations include Lys-Lys, Arg-Arg, Lys-Arg, Arg-Lys, His-His, Val-Val, etc.). These target sequences for mutation are underlined below, where dashes separate the five Ig-binding domains:

```
                                                 (SEQ ID NO: 43)
MKKKNIYSIRKLGVGIASVTLGTLLISGGVTP-AANAAQHDEAQQNAFYQ

VLNMPNLNADQRNGFIQSLKDDPSQSANVLGEAQKLNDSQAPK-ADAQQN

NFNKDQQSAFYEILNMPNLNEAQRNGFIQSLKDDPSQSTNVLGEAKKLNE

SQAPK-ADNNFNKEQQNAFYEILNMPNLNEEQRNGFIQSLKDDPSQSANL

LSEAKKLNESQAPK-ADNKFNKEQQNAFYEILHLPNLNEEQRNGFIQSLK

DDPSQSANLLAEAKKLNDAQAPK-ADNKFNKEQQNAFYEILHLPNLTEEQ

RNGFIQSLKDDPSVSKEILAEAKKLNDAQAPK-EEDNNKPGKEDNNKPGK

EDNNKPGKEDNNKPGKEDNNKPGKEDGNKPGKEDNKKPGKEDGNKPGKED

NKKPGKEDGNKPGKEDGNKPGKEDGNGVHVVKPGDTVNDIAKANGTTADK

IAADNKLADKNMIKPGQELVVDKKQPANHADANKAQALPETGEENPFIGT

TVFGGLSLALGAALLAGRRREL
```

An individual domain within the antigen may be mutated at 1, 2, 3, 4, 5, 6, 7, 8, 9, 10 or more amino acids relative to SEQ ID NO: 43 (e.g. see above in relation to Gln-Gln and Asp-Asp sequences, but also see reference 8 which discloses mutations at residues 3 and/or 24 of domain D, at residue 46 and/or 53 of domain A, etc.). Such mutations should not remove the antigen's ability to elicit an antibody that recognises SEQ ID NO: 43, but will remove the antigen's binding to IgG and/or other human proteins (such as human blood proteins) as noted above. Particularly, the mutant SpA antigen is of sequence comprising or consisting of SEQ ID NO:43 mutated in at least 1, more particularly at least 2, 3, 4, 5, 6, 7, 8, 9, 10, 11, 12, 13, 14, 15, 16, 17, 18, 19 and even more particularly 20 amino acids at position 43, 44, 70, 71, 104, 105, 131, 132, 162, 163, 189, 190, 220, 221, 247, 248, 278, 279, 305 and/or 306 of SEQ ID NO: 43. Useful substitutions for these positions are mentioned above.

Furthermore, the native N-terminus can be removed, and the first 36 amino acids of SEQ ID NO: 43 can usefully be omitted. Similarly, the native C-terminal can be removed, and the sequence downstream of the fifth Ig-binding domain can usefully be omitted (i.e. downstream of Lys-327 in SEQ ID NO: 43). Thus a useful SpA antigen comprises SEQ ID NO: 44:

AQHDEA<u>XX</u>NAFYQVLNMPNLNADQRNGFIQSLK<u>XX</u>PSQSANVLGEAQKLN

DSQAPKADAQQNNFNKD<u>XX</u>SAFYEILNMPNLNEAQRNGFIQSLK<u>XX</u>PSQS

TNVLGEAKKLNESQAPKADNNFNKE<u>XX</u>NAFYEILNMPNLNEEQRNGFIQS

LK<u>XX</u>PSQSANLLSEAKKLNESQAPKADNKFNKE<u>XX</u>NAFYEILHLPNLNEE

QRNGFIQSLK<u>XX</u>PSQSANLLAEAKKLNDAQAPKADNKFNKE<u>XX</u>NAFYEIL

HLPNLTEEQRNGFIQSLK<u>XX</u>PSVSKEILAEAKKLNDAQAPK wherein the 10 underlined XX dipeptides differ from the corresponding dipeptides within SEQ ID NO: 43. Thus a QQ at these positions in SEQ ID NO: 43 will not be QQ in SEQ ID NO: 44, and ideally includes no glutamine residue e.g. it is KK. Similarly, a DD at these positions in SEQ ID NO: 43 will not be DD in SEQ ID NO: 44, and ideally includes no aspartate residue e.g. it is AA. The preferred form of SpA for use with the invention thus comprises SEQ ID NO: 45.

In addition to substitutions at the XX dipeptides in SEQ ID NO: 44 it is possible to modify the amino acid sequence with up to 5 single amino changes provided that the modified sequence can elicit antibodies which still bind to a polypeptide consisting of SEQ ID NO: 44. Thus, SEQ ID NO: 45 can be modified by 1, 2 or 3 substitutions at positions outside the XX dipeptides within SEQ ID NO: 44. For instance, the QQ dipeptide at residues 60-61 of SEQ ID NO: 44 can be mutated to further reduce affinity for immunoglobulins. Useful dipeptide substitutions for a QQ dipeptide are discussed above, and a preferred substitution is KR dipeptide. Thus a useful SpA antigen can comprise SEQ ID NO: 49, in which one or more (preferably all) of the 11 XX dipeptides differ from the corresponding dipeptides within SEQ ID NO: 43. For instance, the SpA antigen can comprise SEQ ID NO: 46, and a preferred example of SEQ ID NO: 46 is SEQ ID NO: 47. When expressed with a N-terminal methionine, the SpA antigen comprising SEQ ID NO: 47 can consist of SEQ ID NO: 48.

As discussed above, a useful fragment of SpA may include only 1, 2, 3 or 4 of the natural A, B, C, D and/or E domains e.g. comprise only the SpA(E) domain but not D, A B or C. Thus a SpA antigen useful with the invention may comprise only the SpA(E) domain mutated as described above, i.e. amino acid sequence comprising or consisting of SEQ ID NO: 54 mutated in at least 1 amino acid at positions 60 and 61 of SEQ ID NO: 54 amino acids 1 to 67 of SEQ ID NO: 44, SEQ ID NO: 45, SEQ ID NO: 46, SEQ ID NO: 47 or SEQ ID NO: 49, or amino acids 1 to 68 of SEQ ID NO: 48. For example, said antigen may comprise SEQ ID NO. 50, SEQ ID NO. 51, SEQ ID NO. 52 or SEQ ID NO. 53. Said antigen will preferably not include other sequence from SpA. It may include more than one copy of the SpA(E) domain, and/or additionally comprise another protein antigen such as an EsxA, EsxB, FhuD2, Sta011, or Hla antigen as described herein.

The antigen combinations of the invention use 1, 2, 3, 4, or all 5 of the following antigens: EsxA; EsxB; FhuD2; Sta011; and Hla. These five antigens are already known in the art (e.g. see references 4-514) and further details are given below. A particularly useful composition includes all five of these antigens (preferably where the Hla is a non-toxic (i.e. detoxified) mutant form).

The 'EsxA' antigen in the NCTC 8325 strain has amino acid sequence SEQ ID NO: 1 (GI:88194063). EsxA antigens used with the present invention can elicit an antibody (e.g. when administered to a human) that recognises SEQ ID NO: 1 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90 or more). These EsxA polypeptides include variants of SEQ ID NO: 1. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1 while retaining at least one epitope of SEQ ID NO: 1.

The 'EsxB' antigen in the NCTC 8325 strain has amino acid sequence SEQ ID NO: 2 (GI:88194070). EsxB used with the present invention can elicit an antibody (e.g. when administered to a human) that recognises SEQ ID NO: 2 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100 or more). These EsxB polypeptides include variants of SEQ ID NO: 2. Preferred fragments of (b) comprise an epitope from SEQ ID NO: 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 2 while retaining at least one epitope of SEQ ID NO: 2. A useful EsxB antigen lacks the internal cysteine residue of SEQ ID NO: 2 e.g. it comprises SEQ ID NO: 35, wherein residue X at position 30 is either absent or is an amino acid residue without a free thiol group (under reducing conditions) e.g. is any natural amino acid except cysteine.

The 'FhuD2' antigen is annotated as 'ferrichrome-binding protein', and has also been studied in the literature [15]. It has also been known as 'Sta006' (e.g. in references 4-14). In the NCTC 8325 strain FhuD2 has amino acid sequence SEQ ID NO: 3 (GI:88196199). FhuD2 used with the present invention can elicit an antibody (e.g. when administered to a human) that recognises SEQ ID NO: 3 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These FhuD2 polypeptides include variants of SEQ ID NO: 3. Preferred fragments of (b) comprise an epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one epitope of SEQ ID NO: 3. The first 17 N-terminal amino acids of SEQ ID NO: 3 can usefully be omitted (to provide SEQ ID NO: 6). Mutant forms of FhuD2 are reported in reference 16. A useful FhuD2 antigen lacks the cysteine residue of SEQ ID NO: 3 e.g. it comprises SEQ ID NO: 34 and does not include any amino acid residue with a free thiol group (under reducing conditions) e.g. it is cysteine-free. A FhuD2 antigen may be lipidated e.g. with an acylated N-terminus cysteine. One useful FhuD2 sequence is SEQ ID NO: 7, which has a Met-Ala-Ser-sequence at the N-terminus; SEQ ID NO: 37 is another such sequence, but it lacks the cysteine present in SEQ ID NO: 7.

The 'Sta011' antigen has amino acid sequence SEQ ID NO: 4 (GI:88193872) in the NCTC 8325 strain. Sta011 antigens used with the invention can elicit an antibody (e.g. when administered to a human) that recognises SEQ ID NO: 4 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). These Sta011 polypeptides include variants of SEQ ID NO: 4. Preferred fragments of (b) comprise an epitope from SEQ ID NO: 4. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 4 while retaining at least one epitope of SEQ ID NO: 4. The first 23 N-terminal amino acids of SEQ ID NO: 4 can usefully be omitted (to provide SEQ ID NO: 33). A useful Sta011 antigen lacks the cysteine residue of SEQ ID NO: 4 e.g. it comprises SEQ ID NO: 36 and does not include any amino acid residue with a free thiol group (under reducing conditions) e.g. it is cysteine-free. A Sta011 antigen may be lipidated e.g. with an acylated N-terminus cysteine. One useful Sta011 sequence is SEQ ID NO: 8, which has a N-terminus methionine; SEQ ID NO: 39 is another such sequence, but it lacks the cysteine present in SEQ ID NO: 8. Variant forms of SEQ ID NO: 4 which may be used as or for preparing Sta011 antigens include, but are not limited to, SEQ ID NOs: 9, 10 and 11 with various Ile/Val/Leu substitutions (and Cys-free variants of these sequences can also be used with the invention). Sta011 can exist as a monomer or an oligomer, with $Ca^{++}$ ions favouring oligomerisation. The invention can use monomers and/or oligomers of Sta011.

The 'Hla' antigen is the 'alpha-hemolysin precursor' also known as 'alpha toxin' or simply 'hemolysin'. In the NCTC 8325 strain Hla has amino acid sequence SEQ ID NO: 5 (GI:88194865). Hla is an important virulence determinant produced by most strains of S. aureus, having pore-forming and haemolytic activity. Anti-Hla antibodies can neutralise the detrimental effects of the toxin in animal models, and Hla is particularly useful for protecting against pneumonia.

Useful Hla antigens can elicit an antibody (e.g. when administered to a human) that recognises SEQ ID NO: 5 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). These Hla antigens include variants of SEQ ID NO: 5. Preferred fragments of (b) comprise an epitope from SEQ ID NO: 5. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 5 while retaining at least one epitope of SEQ ID NO: 5. The first 26 N-terminal amino acids of SEQ ID NO: 5 can usefully be omitted (e.g. to give SEQ ID NO: 12). Truncation at the C-terminus can also be used e.g. leaving only 50 amino acids (residues 27-76 of SEQ ID NO: 5) [17].

Particularly, the Hla antigen is a detoxified Hla antigen, i.e. a mutant form of Hla, wherein Hla's natural toxicity has been removed. Hla's toxicity can be avoided by chemical inactivation (e.g. using formaldehyde, glutaraldehyde or other cross-linking reagents). Instead, however, it is preferred to use mutant forms of Hla which remove its toxic activity while retaining its immunogenicity. More particularly, the detoxified Hla antigen is a mutant form of Hla, wherein Hla's toxicity has been removed while Hla's immunogenicity has been retained. Such detoxified mutants are already known in the art. A preferred Hla antigen is a mutant S. aureus hemolysin having a mutation at residue 61 of SEQ ID NO: 5, which is residue 35 of the mature antigen (i.e. after omitting the first 26 N-terminal amino acids=residue 35 of SEQ ID NO: 12). Thus residue 61 may not be histidine, and may instead be e.g. Ile, Val or preferably Leu. A His-Arg mutation at this position can also be used. For example, SEQ ID NO: 13 is the sequence of the mature H35L mutant form of Hla (i.e. SEQ ID NO: 12 with a H35L mutation) and a useful detoxified Hla antigen is of sequence comprising or consisting of SEQ ID NO: 13. Another useful mutation replaces a long loop with a short sequence e.g. to replace the 39mer at residues 136-174 of SEQ ID NO: 5 with a tetramer such as PSGS (SEQ ID NO: 14), as in SEQ ID NO: 15 (which also includes the H35L mutation) and SEQ ID NO: 16 (which does not include the H35L mutation). Another useful mutation replaces residue Y101 e.g. with a leucine (SEQ ID NO: 17). Another useful mutation replaces residue D152 e.g. with a leucine (SEQ ID NO: 18). Another useful mutant replaces residues H35 and Y101 e.g. with a leucine (SEQ ID NO: 19). Another useful mutant replaces residues H35 and D152 e.g. with a leucine (SEQ ID NO: 20).

Further useful Hla antigens are disclosed in references 18 and 19.

SEQ ID NOs: 21, 22 & 23 are three useful fragments of SEQ ID NO: 5 ('$Hla_{27-76}$', '$Hla_{27-89}$' and '$Hla_{27-79}$', respectively). SEQ ID NOs: 24, 25 & 26 are the corresponding fragments from SEQ ID NO: 13.

One useful Hla sequence is SEQ ID NO: 27. It has a N-terminal Met, then an Ala-Ser dipeptide from the expression vector, then SEQ ID NO: 13 (from NCTC8325 strain) including the H35L mutation.

Where a composition includes both EsxA and EsxB antigens, these may be present as a single polypeptide (i.e. as a fusion polypeptide comprising or consisting of both EsxA and EsxB). Thus a single polypeptide can elicit antibodies (e.g. when administered to a human) that recognise both SEQ ID NO: 1 and SEQ ID NO: 2. The single polypeptide can include: (i) a first polypeptide sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1 and/or comprising a fragment of at least 'n' consecutive amino acids of SEQ ID NO: 1, as defined above for EsxA; and (ii) a second polypeptide sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2 and/or comprising a fragment of at least 'n' consecutive amino acids of SEQ ID NO: 2, as defined above for EsxB. The first and second polypeptide sequences can be in either order, N- to C-terminus. SEQ ID NOs: 28 ('EsxAB') and 29 ('EsxBA') are examples of such polypeptides, both having hexapeptide linkers ASGGGS (SEQ ID NO: 30). Another 'EsxAB' hybrid comprises SEQ ID NO: 31, which may be provided with a N-terminus methionine (e.g. SEQ ID NO: 32). A useful variant of EsxAB lacks the internal cysteine residue of EsxB e.g. it comprises SEQ ID NO: 40 wherein residue X at position 132 is either absent or is an amino acid residue without a free thiol group (under reducing conditions) e.g. is any natural amino acid except cysteine. Thus a preferred EsxAB antigen for use with the invention has amino acid sequence SEQ ID NO: 38.

Thus a useful polypeptide comprises an amino acid sequence (a) having 80% or more identity (e.g. 80%, 85%, 90%, 91%, 92%, 93%, 94%, 95%, 96%, 97%, 98%, 99%, 99.5% or more) to SEQ ID NO: 31; and/or (b) comprising both a fragment of at least 'n' consecutive amino acids from amino acids 1-96 of SEQ ID NO: 31 and a fragment of at least 'n' consecutive amino acids from amino acids 103-205 of SEQ ID NO: 31, wherein 'n' is 7 or more (e.g. 8, 10, 12, 14, 16, 18, 20, 25, 30, 35, 40, 50, 60, 70, 80, 90, 100, 150, 200, 250 or more). These polypeptides (e.g. SEQ ID NO: 32) can elicit antibodies (e.g. when administered to a human) which recognise both the wild-type staphylococcal protein comprising SEQ ID NO: 1 and the wild-type staphylococcal protein comprising SEQ ID NO: 2. Thus the immune response will recognise both of antigens EsxA and EsxB. Preferred fragments of (b) provide an epitope from SEQ ID NO: 1 and an epitope from SEQ ID NO: 2.

The invention uses 1, 2, 3, 4, or all 5 of EsxA, EsxB, FhuD2, Sta011, and Hla (preferably a non-toxic mutant Hla). As mentioned above a particularly useful composition includes all five of these antigens, but in some embodiments the invention includes only 1, 2, 3 or 4 of these five antigens i.e. 1, 2, 3 or 4 of EsxA, EsxB, FhuD2, Sta011, and Hla is absent from the composition.

A preferred composition includes all four of: (i) a single polypeptide including both an EsxA antigen and an EsxB antigen e.g. comprising SEQ ID NO: 31; (ii) a FhuD2 antigen e.g. comprising SEQ ID NO: 6; (iii) a Sta011 antigen e.g. comprising SEQ ID NO: 33; and (iv) a H35L mutant form of Hla e.g. comprising SEQ ID NO: 13.

Although SEQ ID NOs: 31, 6, 33 and 13 are useful amino acid sequences in a combination, the invention is not limited to these precise sequences. Thus 1, 2, 3 or all 4 of these sequences can independently be modified by up to 5 single amino changes (i.e. 1, 2, 3, 4 or 5 single amino acid substitutions, deletions and/or insertions) provided that the modified sequence can elicit antibodies which still bind to a polypeptide consisting of the unmodified sequence.

Another useful composition includes all four of: (i) a first polypeptide having amino acid sequence SEQ ID NO: 32; (ii) a second polypeptide having amino acid sequence SEQ ID NO: 7; (iii) a third polypeptide having amino acid sequence SEQ ID NO: 8; and (iv) a fourth polypeptide having amino acid sequence SEQ ID NO: 27.

Although SEQ ID NOs: 32, 7, 8 and 27 are useful amino acid sequences in a combination, the invention is not limited to these precise sequences. Thus 1, 2, 3 or all 4 of these four sequences can independently be modified by 1, 2, 3, 4 or 5 single amino changes (i.e. 1, 2, 3, 4 or 5 single amino acid substitutions, deletions and/or insertions) provided that the modified sequence can elicit antibodies which still bind to a polypeptide consisting of the unmodified sequence. In a preferred embodiment, a composition thus includes these four specified polypeptides with 1, 2, 3 or all 4 of SEQ ID NO: 32, 7, 8 and 27 independently modified by 1 single amino acid substitution, deletion and/or insertion.

For instance, wild-type FhuD2, Sta011 and EsxAB polypeptide sequences (e.g. SEQ ID NOs: 6, 31 and 33) each include a single cysteine residue which can lead to inter-polypeptide disulfide bridges, forming both homodimers and heterodimers. Such inter-linked polypeptides are undesirable and so Sta006, Sta011 and EsxB sequences can be modified to remove their natural cysteine residues, such that they do not contain free thiol groups (under reducing conditions). The wild-type cysteine can be deleted or can be substituted with a different amino acid.

Thus: a FhuD2 antigen can comprise SEQ ID NO: 34; a Sta011 antigen can comprise SEQ ID NO: 36; and a EsxB antigen can comprise SEQ ID NO: 35 (e.g. as an EsxAB hybrid comprising SEQ ID NO: 40). Examples of such sequences include, but are not limited to, SEQ ID NOs: 37, 39, and 38. These sequences can be used singly as substitutes for the corresponding wild-type sequences, or in combination. Thus a particularly useful composition includes all four of: (i) a first polypeptide having amino acid sequence SEQ ID NO: 38; (ii) a second polypeptide having amino acid sequence SEQ ID NO: 37; (iii) a third polypeptide having amino acid sequence SEQ ID NO: 39; and (iv) a fourth polypeptide having amino acid sequence SEQ ID NO: 27.

Thus a preferred composition of the invention comprises all five of: (i) a single polypeptide including both an EsxA antigen and an EsxB antigen e.g. comprising SEQ ID NO: 31; (ii) a FhuD2 antigen e.g. comprising SEQ ID NO: 6; (iii) a Sta011 antigen e.g. comprising SEQ ID NO: 33; (iv) a H35L mutant form of Hla e.g. comprising SEQ ID NO: 13; and (v) a mutant SpA e.g. comprising SEQ ID NO: 45 or 47, or an antigen comprising a single domain thereof e.g. SEQ ID NO. 50, 51, 52 or 53. So, in particular the composition according to the invention comprises:

(i) a single polypeptide including both an EsxA antigen and an EsxB antigen, particularly of sequence comprising or consisting of SEQ ID NO: 31;
(ii) a FhuD2 antigen, particularly of sequence comprising or consisting of SEQ ID NO: 6;
(iii) a Sta011 antigen, particularly of sequence comprising or consisting of SEQ ID NO: 33;
(iv) a H35L mutant form of Hla, particularly of sequence comprising or consisting of SEQ ID NO: 13; and
(v) a mutant SpA antigen, particularly of sequence comprising or consisting of SEQ ID NO: 45, SEQ ID NO: 47, or SEQ ID NO. 52.

Another preferred composition according to the invention comprises:
(i) a first polypeptide of sequence comprising or consisting of SEQ ID NO: 32, more particularly consisting of SEQ ID NO: 32;

(ii) a second polypeptide of sequence comprising or consisting of SEQ ID NO: 7, more particularly consisting of SEQ ID NO: 7;
(iii) a third polypeptide of sequence comprising or consisting of SEQ ID NO: 8, more particularly consisting of SEQ ID NO: 8;
(iv) a fourth polypeptide of sequence comprising or consisting of SEQ ID NO: 27, more particularly consisting of SEQ ID NO: 27; and
(v) a fifth polypeptide of sequence comprising or consisting of SEQ ID NO. 52, more particularly comprising or consisting of comprising or consisting of SEQ ID NO: 45 modified by up to 3 amino acid substitutions (e.g. comprising SEQ ID NO: 47 or consisting of SEQ ID NO: 48).

Another preferred composition according to the invention comprises:
(i) a first polypeptide of sequence comprising or consisting of SEQ ID NO: 38, more particularly consisting of SEQ ID NO: 38;
(ii) a second polypeptide of sequence comprising or consisting of SEQ ID NO: 37, more particularly consisting of SEQ ID NO: 37;
(iii) a third polypeptide of sequence comprising or consisting of SEQ ID NO: 39, more particularly consisting of SEQ ID NO: 39;
(iv) a fourth polypeptide of sequence comprising or consisting of SEQ ID NO: 27, more particularly consisting of SEQ ID NO: 27; and
(v) a fifth polypeptide of sequence comprising or consisting of SEQ ID NO. 52, more particularly SEQ ID NO: 45 modified by up to 3 amino acid substitutions (e.g. comprising SEQ ID NO: 47 or consisting of SEQ ID NO: 48).

Proteins (i) to (v) in these combinations can, as explained above, independently be modified by up to 5 single amino changes provided that the modified sequence can elicit antibodies which still bind to a polypeptide consisting of the unmodified sequence. In some embodiments, a composition may include one or more further polypeptides; in other embodiments the only polypeptides in a composition are these five specified polypeptides, and these polypeptides can even be the only immunogenic components in a composition.

When more than one polypeptide is present, they may be present at substantially equal masses i.e. the mass of each of them is within ±5% of the mean mass of all the polypeptides. Thus, when five polypeptides are present, they may be present at a mass ratio of a:b:c:d:e, where each of a-e is between 0.95 and 1.05.

Aside from EsxA, EsxB, Hla, FhuD2, Sta011, and SpA, other *S. aureus* antigens exist, and a composition can optionally include one or more further *S. aureus* antigens. For instance, both saccharide and polypeptide antigens are known for *S. aureus*. Thus a composition might include a *S. aureus* saccharide antigen e.g. known saccharide antigens include the exopolysaccharide of *S. aureus*, which is a poly-N-acetylglucosamine (PNAG), and the capsular saccharides of *S. aureus*, which can be e.g. from type 5, type 8 or type 336. A composition might also include a ClfA antigen, an IsdA antigen, an IsdB antigen, an IsdC antigen, and/or an IsdH antigen (each as defined on pages 15-17 of reference 5).

In some embodiments, a composition includes a *S. aureus* antigen as defined above, and also an antigen from a different organism (e.g. from a virus or from another bacterium).

Immunogenic Compositions and Medicaments

Immunogenic compositions according to the invention may be useful as vaccines. Vaccines according to the invention may either be prophylactic (i.e. to prevent infection) or therapeutic (i.e. to treat infection), but will typically be prophylactic.

Compositions may thus be pharmaceutically acceptable. They will usually include components in addition to the antigens e.g. they typically include one or more pharmaceutical carrier(s) and/or excipient(s). A thorough discussion of such components is available in reference 121.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition may be dried, such as a lyophilised formulation. Reference 10 discloses the use of lyophilisation with *S. aureus* immunogenic compositions.

A composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To improve thermal stability, a composition may include a temperature protective agent (see below).

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

Compositions may include a metal ion chelator, in particular a divalent metal ion chelator such as EDTA. Reference 10 discloses that inclusion of EDTA can improve stability of the compositions disclosed herein. The final concentration of EDTA in an immunogenic composition can be about 1-50 mM, about 1-10 mM or about 1-5 mM, preferably about 2.5 mM.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten-free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

*S. aureus* infections can affect various areas of the body and so a composition may be prepared in various forms. For example, a composition may be prepared as injectables, either as liquid solutions or suspensions. Solid forms suitable for solution in, or suspension in, liquid vehicles prior to injection can also be prepared (e.g. a lyophilised composition or a spray-freeze dried composition). A composition may be prepared for topical administration e.g. as an ointment, cream or powder. A composition may be prepared for oral administration e.g. as a tablet or capsule, as a spray, or as a syrup (optionally flavoured). A composition may be prepared for pulmonary administration e.g. as an inhaler, using a fine powder or a spray. A composition may be prepared as a suppository or pessary. A composition may be prepared for nasal, aural or ocular administration e.g. as drops. A composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Human vaccines are typically administered in a dosage volume of about 0.5 ml, although a half volume (i.e. about 0.25 ml) may also be useful e.g. for children.

Immunogenic compositions administered according to the invention may also comprise one or more immunoregulatory agents. Preferably, one or more of the immunoregulatory agents include one or more adjuvants (see below).

The compositions may elicit both a cell mediated immune response as well as a humoral immune response. This immune response will preferably induce long lasting (e.g. neutralising) antibodies and a cell mediated immunity that can quickly respond upon exposure to *S. aureus*.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in reference 20, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da (TEG-300').

Methods of Treatment, and Administration of an Immunogenic Composition

The invention relates to the immunogenic composition according to the invention for use as a medicament.

The invention also relates to the immunogenic composition according to the invention for use as a medicament in the prevention and/or treatment of a *S. aureus* infection.

The invention also provides a method for the prevention and/or treatment of a *S. aureus* infection in a mammal comprising the step of administering to a mammal in need thereof an immunologically effective amount of an immunogenic composition according to the invention as defined above. The advantageous embodiments are as defined above.

The invention also provides the use of (i) at least one antigen selected from the group consisting of EsxA, EsxB, FhuD2, Sta011, and Hla antigens, and (ii) a mutant SpA antigen which has decreased affinity, relative to unmodified SpA, for the Fcγ portion of human IgG and for the Fab portion of $V_H3$-containing human B cell receptors, in the manufacture of a medicament for preventing or treating *S. aureus* infection in a mammal. The advantageous embodiments are as defined above The invention also provides (i) at least one antigen selected from the group consisting of EsxA, EsxB, FhuD2, Sta011, and Hla antigens, and (ii) a mutant SpA antigen which has decreased affinity, relative to unmodified SpA, for the Fcγ portion of human IgG and for the Fab portion of $V_H3$-containing human B cell receptors, for use in immunising a mammal to prevent or treat *S. aureus* infection. The advantageous embodiments are as defined above.

The invention also provides (i) at least one antigen selected from the group consisting of EsxA, EsxB, FhuD2, Sta011, and Hla antigens, and (ii) a mutant SpA antigen which has decreased affinity, relative to unmodified SpA, for the Fcγ portion of human IgG and for the Fab portion of $V_H3$-containing human B cell receptors, for use in a method of immunising a mammal to prevent or treat *S. aureus* infection by administering a therapeutically effective amount of the antigens to the mammal. The advantageous embodiments are as defined above.

As noted above, 1, 2, 3, 4 or preferably all 5 of EsxA, EsxB, FhuD2, Sta011, and Hla can be used in combination with the mutant SpA. In this manner the methods, uses, compositions and antigen combinations of the invention elicit an immune response which is effective for preventing or treating *S. aureus* infections. The immune response can involve antibodies and/or cell-mediated immunity. By raising an immune response in the mammal by these uses and methods, the mammal can be protected against *S. aureus* infection, including a nosocomial infection. More particularly, the mammal may be protected against a skin infection, pneumonia, meningitis, osteomyelitis endocarditis, toxic shock syndrome, and/or septicaemia. The invention is also useful for protecting against *S. aureus* infection of a mammal's bones and joints (and thus for preventing disorders including, but not limited to, osteomyelitis, septic arthritis, and prosthetic joint infection). In many cases these disorders may be associated with the formation of a *S. aureus* biofilm.

*S. aureus* infects various mammals (including cows, dogs, horses, and pigs), but the preferred mammal for use with the invention is a human. The human can be a child (e.g. a toddler or infant), a teenager, or an adult. In some embodiments the human may have a prosthetic bone or joint, or may be an intended recipient of such prostheses (e.g. a pre-operative orthopedic surgery patient). A vaccine intended for children may also be administered to adults e.g. to assess safety, dosage, immunogenicity, etc. The vaccines are not suitable solely for these groups, however, and may be used more generally in a human population.

One way of checking efficacy of therapeutic treatment involves monitoring *S. aureus* infection after administration of the compositions or antigens according to the invention. One way of checking efficacy of prophylactic treatment involves monitoring immune responses, systemically (such as monitoring the level of IgG1 and IgG2a production) and/or mucosally (such as monitoring the level of IgA production), against the antigens in the administered composition after its administration. Another way of assessing the immunogenicity of the compositions is to express the antigens recombinantly for screening patient sera or mucosal secretions by immunoblot and/or microarrays. A positive reaction between the protein and the patient sample indicates that the patient has mounted an immune response to the protein in question.

The efficacy of vaccine compositions can also be determined in vivo by challenging animal models of *S. aureus* infection, e.g., guinea pigs or mice, with the vaccine compositions. There are three generally useful animal models for the study of *S. aureus* infectious disease, namely: (i) the murine abscess model [21], (ii) the murine lethal infection model [21], and (iii) the murine pneumonia model [22]. The abscess model looks at abscesses in mouse kidneys after intravenous challenge. The lethal infection model looks at the number of mice which survive after being infected by a normally-lethal dose of *S. aureus* by the intravenous or intraperitoneal route. The pneumonia model also looks at the survival rate, but uses intranasal infection. Further useful models are disclosed in reference 23 for studying both *S. aureus* disease in relation to biofilm-mediated implant infection, skin and soft tissue infection (SSTI), and sepsis. A useful vaccine may be effective in one or more of these models. For instance, for some clinical situations it may be desirable to protect against pneumonia, without needing to prevent hematic spread or to promote opsonisation; in other situations the main desire may be to prevent hematic spread or sepsis. Different antigens, and different antigen combinations, may contribute to different aspects of an effective vaccine.

Compositions will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration. Intramuscular injection is the most typical route for administering compositions according to the invention.

The invention may be used to elicit systemic and/or mucosal immunity, preferably to elicit an enhanced systemic and/or mucosal immunity. Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Immunogenic compositions may be administered to patients at substantially the same time as (e.g. during the same medical consultation or visit to a healthcare professional or vaccination centre) other vaccines.

Immunogenic compositions may be administered to patients in combination with an antibiotic. For instance, they may be administered at substantially the same time as an antibiotic. Similarly, they may be administered to a subject who is receiving antibiotic therapy. Similarly, they may be administered as part of a co-therapy which involves administration of both a composition as discussed herein and an antibiotic. The antibiotic will be effective against a *S. aureus* bacterium, for instance a beta-lactam.

Strains and Variants

Antigens are discussed above by reference to existing nomenclature (e.g. "EsxA") and exemplary sequences given as GI numbers and also in the sequence listing. The invention is not limited to these precise sequences. Genome sequences of several strains of *S. aureus* are available, including those of MRSA strains N315 and Mu50 [24], MW2, N315, COL, MRSA252, MSSA476, RF122, USA300 (very virulent), JH1, JH9, NCTC 8325, and Newman. Standard search and alignment techniques can be used to identify in any of these (or other) further genome sequences the homolog of any particular sequence mentioned herein Moreover, the specific sequences disclosed herein can be used to design primers for amplification of homologous sequences from other strains. Thus the invention encompasses such variants and homologs from any strain of *S. aureus*, as well as non-natural variants. In general, suitable variants of a particular SEQ ID NO include its allelic variants, its polymorphic forms, its homologs, its orthologs, its paralogs, its mutants, etc.

Thus, for instance, polypeptides used with the invention may, compared to the SEQ ID NO herein, include one or more (e.g. 1, 2, 3, 4, 5, 6, 7, 8, 9, etc.) amino acid substitutions, such as conservative substitutions (i.e. substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, etc.) single amino acid deletions relative to the SEQ ID NO sequences. The polypeptides may also include one or more (e.g. 1, 2, 3, 4, 5, 6, 7, 8, 9, etc.) insertions (e.g. each of 1, 2, 3, 4 or 5 amino acids) relative to the SEQ ID NO sequences.

Similarly, a polypeptide used with the invention may comprise an amino acid sequence that:
- (a) is identical (i.e. 100% identical) to a sequence disclosed in the sequence listing;
- (b) shares sequence identity (e.g. 80%, 85%, 90%, 91%, 92%, 93%, 94%, 95%, 96%, 97%, 98%, 99%, 99.5% or more) with a sequence disclosed in the sequence listing (ideally over the entire length of said sequence);
- (c) has 1, 2, 3, 4, 5, 6, 7, 8, 9 or 10 (or more) single amino acid alterations (deletions, insertions, substitutions), which may be at separate locations or may be contiguous, as compared to the sequences of (a) or (b); or
- (d) when aligned with a particular sequence from the sequence listing using a pairwise alignment algorithm, each moving window of x amino acids from N-terminus to C-terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [25], using default parameters (e.g. with Gap opening penalty=10.0, and with Gap extension penalty=0.5, using the EBLOSUM62 scoring matrix). This algorithm is conveniently implemented in the needle tool in the EMBOSS package [26].

Where hybrid polypeptides are used, the individual antigens within the hybrid (i.e. individual -X-moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus. N-terminus truncation can remove leader peptides e.g. to facilitate recombinant expression in a heterologous host. C-terminus truncation can remove anchor sequences e.g. to facilitate recombinant expression in a heterologous host.

In general, when an antigen comprises a sequence that is not identical to a complete *S. aureus* sequence from the sequence listing (e.g. when it comprises a sequence listing with <100% sequence identity thereto, or when it comprises a fragment thereof) it is preferred in each individual instance that the antigen can elicit an antibody which recognises the respective complete *S. aureus* sequence.

Polypeptides Used with the Invention

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, etc.).

Polypeptides used with the invention can be prepared by various means (e.g. recombinant expression, purification from cell culture, chemical synthesis, etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other staphylococcal or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

Although expression of the polypeptides of the invention may take place in a *Staphylococcus*, the invention will usually use a heterologous host for expression (recombinant expression). The heterologous host may be prokaryotic (e.g. a bacterium) or eukaryotic. It may be *E. coli*, but other suitable hosts include *Bacillus subtilis, Vibrio cholerae, Salmonella typhi, Salmonella typhimurium, Neisseria lactamica, Neisseria cinerea*, Mycobacteria (e.g. *M. tuberculosis*), yeasts, etc. Compared to the wild-type *S. aureus* genes encoding polypeptides of the invention, it is helpful to change codons to optimise expression efficiency in such hosts without affecting the encoded amino acids.

Adjuvants

As mentioned above, immunogenic compositions used according to the invention may include one or more adjuvants. Adjuvants which may be used with the invention include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in ref. 27). Aluminum salts include hydroxides and phosphates etc., with the salts taking any suitable form (e.g. gel, crystalline, amorphous, etc.). Adsorption to these salts is preferred (e.g. all antigens may be adsorbed). The mineral containing compositions may also be formulated as a particle of metal salt [28].

The adjuvants known as aluminum hydroxide and aluminum phosphate may be used. These names are conventional, but are used for convenience only, as neither is a precise description of the actual chemical compound which is present (e.g. see chapter 9 of reference 29). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4/Al$ molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

B. Oil-in-Water Emulsions

Oil-in-water emulsion compositions suitable for use as adjuvants in the invention include squalene-in-water emulsions, such as MF59 (see Chapter 10 of ref. 29; see also ref. 30) and AS03 [31].

Various oil-in-water emulsion adjuvants are known, and they typically include at least one oil and at least one surfactant, with the oil(s) and surfactant(s) being biodegradable (metabolisable) and biocompatible. The emulsion will include submicron oil droplets, and emulsions with droplets having a diameter less than 220 nm are preferred as they can be subjected to filter sterilization.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolisable and so may be used. The procedures for separation, purification, saponification and other means necessary for obtaining pure oils from animal sources are well known in the art.

Most fish contain metabolisable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Preferred emulsions comprise squalene, a shark liver oil which is a branched, unsaturated terpenoid. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g. DL-α-tocopherol) can be used.

The oil in the emulsion may comprise a combination of oils e.g. squalene and at least one other oil.

The aqueous component of the emulsion can be plain water (e.g. w.f.i.) or can include further components e.g. solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin and Triton X-100.

Mixtures of surfactants can be used e.g. Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8).

Preferred amounts of oil (% by volume) in the final emulsion are between 2-20% e.g. 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm e.g. less than 200 nm, less than 150 nm. The average droplet size is usefully in the range of 80-180 nm. Ideally, at least 80% (by number) of the emulsion's oil droplets are less than 250 nm in diameter, and preferably at least 90%. These droplet sizes can conveniently be achieved by techniques such as microfluidisation. Apparatuses for determining the average droplet size in an emulsion, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan).

Ideally, the distribution of droplet sizes (by number) has only one maximum i.e. there is a single population of droplets distributed around an average (mode), rather than having two maxima. Preferred emulsions have a polydispersity of <0.4 e.g. 0.3, 0.2, or less.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [32-34], as described in more detail in Chapter 10 of ref. 35 and chapter 12 of ref. 36. The MF59 emulsion advantageously includes citrate ions e.g. 10 mM sodium citrate buffer.

An emulsion comprising squalene, a tocopherol, and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL a tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [37] e.g. in the ratios discussed above.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [38] (0.05-1% Thr-MDP, 5% squalane, 2.5% Pluronic L121 and 0.2% polysorbate 80). It can also be used without the Thr-MDP, as in the "AF" adjuvant [39] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monooleate or 'Span 80'). The emulsion is preferably thermoreversible and/or has at least 90% of the oil droplets (by volume) with a size less than 200 nm [40]. The emulsion may also include one or more of: alditol; a cryoprotective agent (e.g. a sugar, such as dodecylmaltoside and/or sucrose); and/or an alkylpolyglycoside. The emulsion may include a TLR4 agonist [41]. Such emulsions may be lyophilized.

An emulsion of squalene, poloxamer 105 and Abil-Care [42]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 43, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 44, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion in which a saponin (e.g. QuilA or QS21) and a sterol (e.g. a cholesterol) are associated as helical micelles [45].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [46].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [46].

In some embodiments an emulsion may be mixed with antigen(s) extemporaneously, at the time of delivery, and thus the adjuvant and antigen(s) may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

C. Saponin Formulations [Chapter 22 of Ref 29]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 47. Saponin formulations may also comprise a sterol, such as cholesterol [48].

Combinations of saponins and cholesterols can be used to form particles called ISCOMs (chapter 23 of ref. 29). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 48-50. Optionally, the ISCOMS may be devoid of additional detergent [51].

A review of the development of saponin based adjuvants can be found in refs. 52 & 53.

D. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 54. Such "small particles" of 3dMPL are small enough to be sterile filtered through a 0.22 µm membrane [54]. Other non-toxic LPS derivatives include monophosphoryl lipid A mimics, such as aminoalkyl glucosaminide phosphate derivatives e.g. RC-529 (see below).

Lipid A derivatives include derivatives of lipid A from *Escherichia coli* such as OM-174. OM-174 is described for example in refs. 55 & 56.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 57, 58 and 59 disclose possible analog substitutions e.g. replacement of guanosine with 2'-deoxy-7-deazaguanosine. The adjuvant effect of CpG oligonucleotides is further discussed in refs. 60-65.

The CpG sequence may be directed to TLR9, such as the motif GTCGTT or TTCGTT [66]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 67-69. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 66 & 70-72.

A useful CpG adjuvant is CpG7909, also known as ProMune™ (Coley Pharmaceutical Group, Inc.). Another is CpG1826. As an alternative, or in addition, to using CpG sequences, TpG sequences can be used [73], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. 73), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 73), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC-31™ [74]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 41). The polycationic polymer may be a peptide comprising 11-mer amino acid sequence KLKLLLLLKLK (SEQ ID NO: 42). The oligonucleotide and polymer can form complexes e.g. as disclosed in references 75 & 76.

Bacterial ADP-ribosylating toxins and detoxified derivatives thereof may be used as adjuvants in the invention. Preferably, the protein is derived from E. coli (E. coli heat labile enterotoxin "LT"), cholera ("CT"), or pertussis ("PT"). The use of detoxified ADP-ribosylating toxins as mucosal adjuvants is described in ref. 77 and as parenteral adjuvants in ref. 78. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 79-86. A useful CT mutant is or CT-E29H [87]. Numerical reference for amino acid substitutions is preferably based on the alignments of the A and B subunits of ADP-ribosylating toxins set forth in ref. 88, specifically incorporated herein by reference in its entirety.

E. TLR Agonists

Compositions can include a TLR agonist i.e. a compound which can agonise a Toll-like receptor. Most preferably, a TLR agonist is an agonist of a human TLR. The TLR agonist can activate any of TLR1, TLR2, TLR3, TLR4, TLR5, TLR6, TLR7, TLR8, TLR9 or TLR11; preferably it can activate human TLR4 or human TLR7.

Agonist activity of a compound against any particular Toll-like receptor can be determined by standard assays. Companies such as Imgenex and Invivogen supply cell lines which are stably co-transfected with human TLR genes and NFκB, plus suitable reporter genes, for measuring TLR activation pathways. They are designed for sensitivity, broad working range dynamics and can be used for high-throughput screening. Constitutive expression of one or two specific TLRs is typical in such cell lines. See also reference 89. Many TLR agonists are known in the art e.g. reference 90 describes certain lipopeptide molecules that are TLR2 agonists, references 91 to 94 each describe classes of small molecule agonists of TLR7, and references 95 & 96 describe TLR7 and TLR8 agonists for treatment of diseases.

A TLR agonist used with the invention ideally includes at least one adsorptive moiety. The inclusion of such moieties in TLR agonists allows them to adsorb to insoluble aluminium salts (e.g. by ligand exchange or any other suitable mechanism) and improves their immunological behaviour [97]. Phosphorus-containing adsorptive moieties are particularly useful, and so an adsorptive moiety may comprise a phosphate, a phosphonate, a phosphinate, a phosphonite, a phosphinite, etc. Preferably the TLR agonist includes at least one phosphonate group.

Thus, in preferred embodiments, a composition includes a TLR agonist (more preferably a TLR7 agonist) which includes a phosphonate group. This phosphonate group can allow adsorption of the agonist to an insoluble aluminium salt [97].

TLR agonists useful with the invention may include a single adsorptive moiety, or may include more than one e.g. between 2 and 15 adsorptive moieties. Typically a compound will include 1, 2 or 3 adsorptive moieties.

Useful phosphorus-containing TLR agonists can be represented by formula (A1):

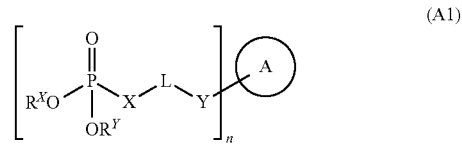

(A1)

wherein:
R$^X$ and R$^Y$ are independently selected from H and C$_1$-C$_6$ alkyl;
X is selected from a covalent bond, O and NH;
Y is selected from a covalent bond, O, C(O), S and NH;
L is a linker e.g. selected from, C$_1$-C$_6$alkylene, C$_1$-C$_6$alkenylene, arylene, heteroarylene, C$_1$-C$_6$alkyleneoxy and —((CH$_2$)$_p$O)$_q$(CH$_2$)$_p$— each optionally substituted with 1 to 4 substituents independently selected from halo, OH, C$_1$-C$_4$alkyl, —OP(O)(OH)$_2$ and —P(O)(OH)$_2$;
each p is independently selected from 1, 2, 3, 4, 5 and 6;
q is selected from 1, 2, 3 and 4;
n is selected from 1, 2 and 3; and
A is a TLR agonist moiety.

In one embodiment, the TLR agonist according to formula (A1) is as follows: R$^X$ and R$^Y$ are H; X is O; L is selected from C$_1$-C$_6$ alkylene and —((CH$_2$)$_p$O)$_q$(CH$_2$)$_p$— each optionally substituted with 1 to 2 halogen atoms; p is selected from 1, 2 and 3; q is selected from 1 and 2; and n is 1. Thus in these embodiments the adsorptive moiety comprises a phosphate group.

Other useful TLR agonists of formula (A1) are disclosed on pages 6-13 of reference 98.

Compositions can include an imidazoquinolone compound, such as Imiquimod ("R-837") [99,100], Resiquimod ("R-848") [101], and their analogs; and salts thereof (e.g. the hydrochloride salts). Further details about immunostimulatory imidazoquinolines can be found in references 102 to 106.

Compositions can include a TLR4 agonist, and most preferably an agonist of human TLR4. TLR4 is expressed by cells of the innate immune system, including conventional dendritic cells and macrophages [107]. Triggering via TLR4 induces a signalling cascade that utilizes both the MyD88- and TRIF-dependent pathways, leading to NF-κB and IRF3/7 activation, respectively. TLR4 activation typically induces robust IL-12p70 production and strongly enhances Th1-type cellular and humoral immune responses.

Various useful TLR4 agonists are known in the art, many of which are analogs of endotoxin or lipopolysaccharide (LPS). For instance, the TLR4 agonist can be: 3d-MPL (i.e. 3-O-deacylated monophosphoryl lipid A; present in GSK's 'AS04' adjuvant, with further details in references 108 to 111 glucopyranosyl lipid A (GLA) [112] or its ammonium salt; an aminoalkyl glucosaminide phosphate, such as RC-529 or CRX-524 [113-115]; E5564 [116,117]; or a compound of formula I, II or III as defined in reference 118, or a salt thereof, such as compounds 'ER 803058', 'ER 803732', 'ER 804053', 'ER 804058', 'ER 804059', 'ER 804442', 'ER 804680', 'ER 803022', 'ER 804764' or 'ER 804057' (also known as E6020).

The invention is particularly useful when using human TLR7 agonists, such as a compound of formula (K). These agonists are discussed in detail in reference 119:

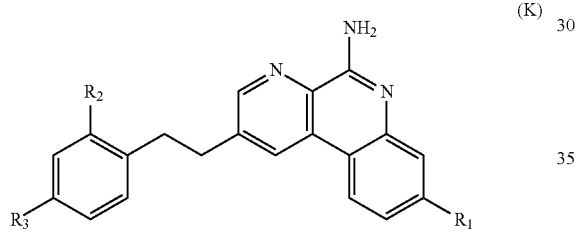

(K)

wherein:

$R^1$ is H, $C_1$-$C_6$alkyl, —$C(R^5)_2$OH, -$L^1R^5$, -$L^1R^6$, -$L^2R^5$, -$L^2R^6$, -O$L^2R^5$, or -O$L^2R^6$;

$L^1$ is —C(O)— or —O—;

$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;

each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;

$L^4$ is arylene or heteroarylene;

$R^2$ is H or $C_1$-$C_6$alkyl;

$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, - O$L^3R^5$, —O$L^3R^7$, -O$L^3L^4R^7$, -O$L^3L^4L^3R^7$, —$OR^8$, -O$L^3L^4R^5$, -O$L^3L^4L^3R^5$ and —$C(R^5)_2$OH;

each $R^4$ is independently selected from H and fluoro;

$R^5$ is —$P(O)(OR^9)_2$, $R^6$ is —$CF_2P(O)(OR^9)_2$ or —$C(O)OR^{10}$;

$R^7$ is —$CF_2P(O)(OR^9)_2$ or —$C(O)OR^{10}$;

$R^8$ is H or $C_1$-$C_4$alkyl;

each $R^9$ is independently selected from H and $C_1$-$C_6$alkyl;

$R^{10}$ is H or $C_1$-$C_4$alkyl;

each p is independently selected from 1, 2, 3, 4, 5 and 6, and q is 1, 2, 3 or 4.

The compound of formula (K) is preferably of formula (K):

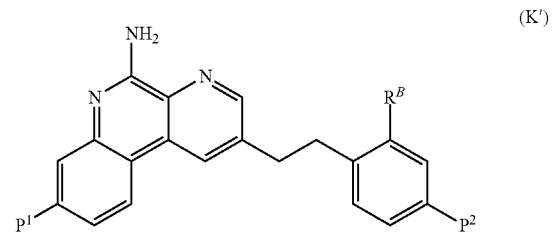

(K')

wherein:

$P^1$ is selected from H, $C_1$-$C_6$alkyl optionally substituted with COOH and —Y-L-X—$P(O)(OR^X)(OR^Y)$;

$P^2$ is selected from H, $C_1$-$C_6$alkyl, $C_1$-$C_6$alkoxy and —Y-L-X—$P(O)(OR^X)(OR^Y)$;

with the proviso that at least one of $P^1$ and $P^2$ is —Y-L-X—$P(O)(OR^X)(OR^Y)$;

$R^B$ is selected from H and $C_1$-$C_6$alkyl;

$R^X$ and $R^Y$ are independently selected from H and $C_1$-$C_6$alkyl;

X is selected from a covalent bond, O and NH;

Y is selected from a covalent bond, O, C(O), S and NH;

L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;

each p is independently selected from 1, 2, 3, 4, 5 and 6; and q is selected from 1, 2, 3 and 4.

In some embodiments of formula (IC): $P^1$ is selected from $C_1$-$C_6$alkyl optionally substituted with COOH and —Y-L-X—$P(O)(OR^X)(OR^Y)$; $P^2$ is selected from $C_1$-$C_6$alkoxy and —Y-L-X—$P(O)(OR^X)(OR^Y)$; $R^B$ is $C_1$-$C_6$alkyl; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

A preferred compound of formula (K) for use with the invention is 3-(5-amino-2-(2-methyl-4-(2-(2-(2-phosphonoethoxy) ethoxy)ethoxy)phenethyl)benzo[f][1,7]naphthyridin-8-yl)propanoic acid, or compound 'K1':

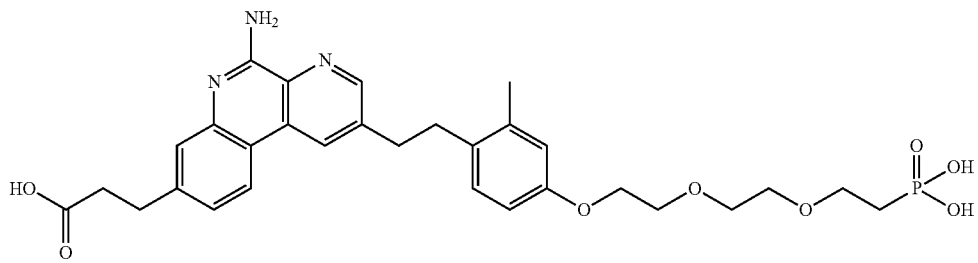

(K1)

This compound can be used as free base or in the form of a pharmaceutically acceptable salt e.g. an arginine salt [120].

F. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Adjuvant Combinations

The individual adjuvants listed above may also be included in combinations. For instance, a combination of an aluminium hydroxide and an aluminium phosphate adjuvant can be used. Similarly, a combination of aluminium phosphate and 3dMPL may be used.

A particularly preferred adjuvant combination is an insoluble metal salt (e.g. an aluminium salt, such as an aluminium hydroxide) and a TLR agonist (e.g. a human TLR7 agonist, such as compound 'K1' identified above), as disclosed in references 5 and 97. So, in particular, said adjuvant is selected from the group consisting of:

aluminium salts, particularly aluminium hydroxides and aluminium phosphates;
human TLR agonists, particularly TLR7 agonists; and
a mixture thereof.

The TLR agonist is preferably adsorbed to the metal salt, and the S. aureus antigen(s) can also be adsorbed to the metal salt.

A composition including a TLR agonist of the invention adsorbed to a metal salt can also include a buffer (e.g. a phosphate or a histidine or a Tris buffer). When such a composition includes a phosphate buffer, however, it is preferred that the concentration of phosphate ions in the buffer should be less than 50 mM e.g. <40 mM, <30 mM, <20 mM, <10 mM, or <5 mM, or between 1-15 mM. A histidine buffer is preferred e.g. between 1-50 mM, between 5-25 mM, or about 10 mM.

A composition can include a mixture of both an aluminium oxyhydroxide and an aluminium hydroxyphosphate, and a TLR agonist may be adsorbed to one or both of these salts.

As mentioned above, a maximum of 0.85 mg/dose $Al^{+++}$ is preferred. Because the inclusion of a TLR agonist can improve the adjuvant effect of aluminium salts then the invention advantageously permits lower amounts of $Al^{+++}$ per dose, and so a composition can usefully include between 10 and 250 μg of $Al^{+++}$ per unit dose. Current pediatric vaccines typically include at least 300 μg $Al^{+++}$. In concentration terms, a composition may have an $Al^{+++}$ concentration between 10 and 500 μg/ml e.g. between 10-300 μg/ml, between 10-200 μg/ml, or between 10-100n/ml.

In general, when a composition includes both a TLR agonist and an aluminium salt, the weight ratio of agonist to $Al^{+++}$ will be less than 5:1 e.g. less than 4:1, less than 3:1, less than 2:1, or less than 1:1. Thus, for example, with an $Al^{+++}$ concentration of 0.5 mg/ml the maximum concentration of TLR agonist would be 1.5 mg/ml. But higher or lower levels can be used.

Where a composition includes a TLR agonist and an insoluble metal salt, it is preferred that at least 50% (by mass) of the agonist in the composition is adsorbed to the metal salt e.g. ≥60%, ≥70%, ≥80%, ≥85%, ≥90%, ≥92%, ≥94%, ≥95%, ≥96%, ≥97%, ≥98%, ≥99%, or even 100%.

Thus, in one embodiment, the invention uses an immunogenic composition comprising:

an aluminium hydroxide adjuvant;
a TLR7 agonist of formula (K), such as compound K1;
a first polypeptide comprising SEQ ID NO: 6, or a modified amino acid sequence which differs from SEQ ID NO: 6 by up to 5 single amino changes provided that the modified sequence can elicit antibodies which bind to a polypeptide consisting of SEQ ID NO: 6;
a second polypeptide comprising SEQ ID NO: 13, or a modified amino acid sequence which differs from SEQ ID NO: 13 by up to 5 single amino changes provided that the modified sequence can elicit antibodies which bind to a polypeptide consisting of SEQ ID NO: 13;
a third polypeptide comprising SEQ ID NO: 31, or a modified amino acid sequence which differs from SEQ ID NO: 31 by up to 5 single amino changes provided that the modified sequence can elicit antibodies which bind to a polypeptide consisting of SEQ ID NO: 31;
a fourth polypeptide comprising SEQ ID NO: 33, or a modified amino acid sequence which differs from SEQ ID NO: 33 by up to 5 single amino changes provided that the modified sequence can elicit antibodies which bind to a polypeptide consisting of SEQ ID NO: 33; and
a fifth polypeptide comprising SEQ ID NO: 45, or a modified amino acid sequence which differs from SEQ ID NO: 45 by up to 5 single amino changes provided that the modified sequence can elicit antibodies which bind to a polypeptide consisting of SEQ ID NO: 43; and,
in which the TLR7 agonist and/or at least one of the polypeptides is/are adsorbed to the aluminium hydroxide adjuvant.

For example, as explained in more detail elsewhere herein: the first polypeptide can comprise SEQ ID NO: 34; the second polypeptide can comprise SEQ ID NO: 13; the third polypeptide can comprise SEQ ID NO: 40; the fourth polypeptide can comprise SEQ ID NO: 36; and the fifth polypeptide can comprise SEQ ID NO: 45, optionally modified by up to 3 amino acid substitutions (other than at positions which are X in SEQ ID NO: 44). Thus the composition can use a mixture of five polypeptides having SEQ ID NOs: 37, 27, 38, 39, and 45 (except that SEQ ID NO: 45 can be modified by up to 3 amino acid substitutions as discussed above).

Chemical Groups

Unless specifically defined elsewhere, the chemical groups discussed herein have the following meaning when used in present specification:

The term "alkyl" includes saturated hydrocarbon residues including:
- linear groups up to 10 atoms ($C_1$-$C_{10}$), or of up to 6 atoms ($C_1$-$C_6$), or of up to 4 atoms ($C_1$-$C_4$). Examples of such alkyl groups include, but are not limited to, $C_1$-methyl, $C_2$-ethyl, $C_3$-propyl and $C_4$-n-butyl.
- branched groups of between 3 and 10 atoms ($C_3$-$C_{10}$), or of up to 7 atoms ($C_3$-$C_7$), or of up to 4 atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

The term "alkylene" refers to the divalent hydrocarbon radical derived from an alkyl group, and shall be construed in accordance with the definition above.

The term "alkenyl" includes monounsaturated hydrocarbon residues including:
- linear groups of between 2 and 6 atoms ($C_2$-$C_6$). Examples of such alkenyl groups include, but are not limited to, $C_2$-vinyl, $C_3$-1-propenyl, $C_3$-allyl, $C_4$-2-butenyl
- branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl.

The term alkenylene refers to the divalent hydrocarbon radical derived from an alkenyl group, and shall be construed in accordance with the definition above.

The term "alkoxy" includes O-linked hydrocarbon residues including:
- linear groups of between 1 and 6 atoms ($C_1$-$C_6$), or of between 1 and 4 atoms ($C_1$-$C_4$). Examples of such alkoxy groups include, but are not limited to, $C_1$-methoxy, $C_2$-ethoxy, $C_3$-n-propoxy and $C_4$-n-butoxy.
- branched groups of between 3 and 6 atoms ($C_3$-$C_6$) or of between 3 and 4 atoms ($C_3$-$C_4$). Examples of such alkoxy groups include, but are not limited to, $C_3$-iso-propoxy, and $C_4$-sec-butoxy and tert-butoxy.

Halo is selected from Cl, F, Br and I. Halo is preferably F.

The term "aryl" includes a single or fused aromatic ring system containing 6 or 10 carbon atoms; wherein, unless otherwise stated, each occurrence of aryl may be optionally substituted with up to 5 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined above. Typically, aryl will be optionally substituted with 1, 2 or 3 substituents. Optional substituents are selected from those stated above. Examples of suitable aryl groups include phenyl and naphthyl (each optionally substituted as stated above). Arylene refers the divalent radical derived from an aryl group, and shall be construed in accordance with the definition above.

The term "heteroaryl" includes a 5, 6, 9 or 10 membered mono- or bi-cyclic aromatic ring, containing 1 or 2 N atoms and, optionally, an $NR^{14}$ atom, or one $NR^{14}$ atom and an S or an O atom, or one S atom, or one O atom; wherein, unless otherwise stated, said heteroaryl may be optionally substituted with 1, 2 or 3 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined below. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Heteroarylene refers the divalent radical derived from heteroaryl, and shall be construed in accordance with the definition above.

The term "heterocyclyl" is a C-linked or N-linked 3 to 10 membered non-aromatic, mono- or bi-cyclic ring, wherein said heterocycloalkyl ring contains, where possible, 1, 2 or 3 heteroatoms independently selected from N, $NR^{14}$, $S(O)_q$ and O; and said heterocycloalkyl ring optionally contains, where possible, 1 or 2 double bonds, and is optionally substituted on carbon with 1 or 2 substituents independently selected from ($C_1$-$C_6$)alkyl, ($C_1$-$C_6$)alkoxy, OH, CN, $CF_3$, halo, $COOR^{14}$, $NR^{14}R^{15}$ and aryl.

In the above definitions $R^{14}$ and $R^{15}$ are independently selected from H and ($C_1$-$C_6$)alkyl.

When a structural formula is defined with a substituent attached to the core of the molecule by an unspecified, or "floating" bond, for example, as for the group $P^3$ in the case of formula (C), this definition encompasses the cases where the unspecified substituent is attached to any of the atoms on the ring in which the floating bond is located, whilst complying with the allowable valence for that atom.

In the case of compounds of the invention which may exist in tautomeric forms (i.e. in keto or enol forms), for example the compounds of formula (C) or (H), reference to a particular compound optionally includes all such tautomeric forms.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 121-128, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN [129,130] or similar methods), or they can be predicted (e.g. using the Jameson-Wolf antigenic index [131], matrix-based approaches [132], MAPITOPE [133], TEPITOPE [134, 135], neural networks [136], OptiMer & EpiMer [137, 138], ADEPT [139], Tsites [140], hydrophilicity [141], antigenic index [142] or the methods disclosed in references 143-147, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 148. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 149. Percentage identity to any particular sequence (e.g. to a particular SEQ ID) is ideally calculated over the entire length of that sequence.

Binding affinity may be determined by any method known in the art, including surface plasmon resistance, isothermal titration calorimetry, competitive binding assays, thermal shift assay, etc. Although the absolute figures obtained using different methods may vary, it is envisaged that the determination relative binding affinity of one protein compared to another should not depend on the method used.

Phosphorous-containing adjuvants used with the invention may exist in a number of protonated and deprotonated forms depending on the pH of the surrounding environment, for example the pH of the solvent in which they are dissolved. Therefore, although a particular form may be illustrated, it is intended that these illustrations are merely representative and not limiting to a specific protonated or deprotonated form. For example, in the case of a phosphate group, this has been illustrated as —OP(O)(OH)$_2$ but the definition includes the protonated forms [OP(O)(OH$_2$)(OH)]$^+$ and —[OP(O)(OH)$_2$]$^{2+}$ that may exist in acidic conditions and the deprotonated forms —[OP(O)(OH)(O)]$^-$ and [OP(O)(O)$_2$]$^{2-}$ that may exist in basic conditions.

Compounds can exist as pharmaceutically acceptable salts. Thus, compounds (e.g. adjuvants) may be used in the form of their pharmaceutically acceptable salts i.e. physiologically or toxicologically tolerable salt (which includes, when appropriate, pharmaceutically acceptable base addition salts and pharmaceutically acceptable acid addition salts).

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

SpAkR Mutant

SpA is a crucial virulence factor in *S. aureus* and it acts by interfering with opsonophagocytic clearance of the bacterium and by ablating adaptive immune responses. The wild-type sequence SEQ ID NO: 43 includes five Ig-binding domains (IgBD), as shown above, and it is known to mutate amino acid residues within these domains to abolish Fc/Fab binding activity while retaining immunogenicity e.g. see reference 9, which replaces Gln-Gln dipeptides with Lys-Lys and/or replaces Asp-Asp dipeptides with Ala-Ala.

A new mutant SpA has been produced in which a further Gln-Gln dipeptide is mutated to Lys-Arg. This dipeptide was identified based on bioinformatics analysis and predictions of an additional site involved in Ig binding. In particular, residues 96 & 97 of SEQ ID NO: 43 were hypothesised to be involved in Ig binding. This site was overlooked in earlier work because it is outside the conserved IgBD and is not part of the solved structures. The new mutant is referred to as 'SpAkR' and it has the following amino acid sequence, where the extra QQ/KR substitution relative to the previous 'SpAkkAA' mutant is boxed:

```
                                         (SEQ ID NO: 48)
MAQHDEAKKNAFYQVLNMPNLNADQRNGFIQSLKAAPSQSANVLGEAQKL
NDSQAPKADAKRNNFNKDKKSAFYEILNMPNLNEAQRNGFIQSLKAAPSQ
STNVLGEAKKLNESQAPKADNNFNKEKKNAFYEILNMPNLNEEQRNGFIQ
SLKAAPSQSANLLSEAKKLNESQAPKADNKFNKEKKNAFYEILHLPNLNE
EQRNGFIQSLKAAPSQSANLLAEAKKLNDAQAPKADNKFNKEKKNAFYEI
LHLPNLTEEQRNGFIQSLKAAPSVSKEILAEAKKLNDAQAPK
```

The SpAkR mutant has been confirmed to have reduced affinity for immunoglobulins relative to known mutants, while retaining immunogenicity.

CD and DSC analysis showed that the introduction of the KR mutant did not materially affect the structure of SpA. The CD spectra of SpAkkAA and SpAKR were identical. $T_m1$ and $T_m2$ from DSC analysis were as follows. $T_m1$: SpAkkAA 48.9° C.; SpAKR 51.1° C. $T_m2$: SpAkkAA 68.1° C.; SpAKR 68.0° C.

Affinity of wild-type SpA, and of the SpAkkAA and SpAkR mutants, for human IgG, IgA and IgM was tested using surface plasmon resonance. The proteins were immobilized on a sensor chip and human IgG, IgA and IgM were used as analytes. Both mutants displayed a greatly reduced binding capacity compared to wild-type, but while SpAkkAA showed residual binding to IgG and IgM, no detectable interactions with any immunoglobulins were seen with SpAkR. Residual binding activities of SpAkkAA towards IgG and IgM were very low (11-12-fold lower than wild-type), but reproducible and concentration-dependent.

*S. aureus* survival in the presence of SpA (WT, SpAkkAA and SpAkR) was assessed through whole blood survival assay (WBA). 1 ml whole blood from healthy donors, supplemented with 50 mg/l lepirudin anticoagulant (10 μl/ml blood), was inclubated with 0.15 μM SpA or with PBS, for 15 min at 37° C., before adding approximately $2.5\times10^5$ CFU of *S. aureus* USA300 LAC ($OD_{600}$, 0.4) diluted in BHI. Aliquots of this culture were plated on BHI-agar to determine the input CFU. After incubation at 37° C. for 2 h with shaking (180 RPM), neutrophils were lysed at 0.5% saponin-PBS for 3 min on ice. The number of viable bacteria was determined by serial tenfold dilutions in BHI and plating on nutrient agar plates. Colonies were counted after incubation of the plates at 37° C. for 18 h. Control was the blood sample preincubated with PBS. Relative survival was calculated based on the input CFU compared to CFU post-incubation. Experiments were performed in triplicate; there was little variation between the experiments.

In the WBA, relative survival of *S. aureus* in human whole blood was considerably lower when incubated with SpAKR than with wild type SpA ($p<0.001$, Mann-Whitney) or with SpAkkAA ($p<0.05$). Incubation with SpAwt resulted in increased *S. aureus* survival compared to control ($p<0.001$), whereas survival in WBA incubated with SpAkkAA was comparable to control. Incubation with SpAkR reduced survival to about half of that of the control.

SpAkkAA or SpAkR formulated with aluminium hydroxide adjuvant were found to be weakly immunogenic in mice on their own, but inclusion of adsorbed TLR7 agonist 'K1' significantly increased antibody titres. Because the mechanism of action associated with SpA immunisation appears to be mainly driven by antibodies, this is an important improvement.

S. aureus Vaccines

SpAkR, SpAkkAA, SpAkR E domain alone and SpAkR E domain fused to HlaH35L were tested in the renal abscess model, adjuvanted with aluminium hydroxide (Al—H) at 2 mg/ml (total salt). Antigens were each present at 10 μg in a 100 μL dose for intramuscular injection.

Four or five-week old mice (CD1) were immunized intramuscularly (IM) with prime-booster injections with a 14-day interval. Control mice received equal amounts of adjuvants alone. Serum was collected from mice both pre- and post-vaccination to document serum antibody titers to each protein component in the combination vaccine. These titers were measured by Luminex technology using the recombinant vaccine antigens conjugated to microspheres.

Renal Abscess Model:

Immunized animals were challenged on day 24 by intravenous injection of a sublethal dose of S. aureus Newman strain (~2-6×10$^7$ CFU). On day 28, mice were euthanized and kidneys were removed and homogenized in 2 mL of PBS and plated on agar media in duplicate for determination of colony forming units (CFU).

A comparable reduction in $\log_{10}$ CFU/ml (around 1 log reduction) was obtained on vaccination with SpAKR, SpAk-kAA, SpAkR E domain alone and SpAkR E domain fused to HlaH35L, compared to adjuvant alone.

Combination S. aureus Vaccines

A 5-valent and a 6-valent vaccine were prepared. The 5-valent vaccine included antigens consisting of SEQ ID NOs: 7, 8, 27 and 32 (FhuD2, Sta011, Hla-H35L, and EsxAB); the 6-valent vaccine also included the SpAkR mutant. The vaccines were adjuvanted with: (i) aluminium hydroxide, Al—H; (ii) Al—H+adsorbed TLR7 agonist K1; or (iii) the oil-in-water emulsion MF59. Al—H was used at 2 mg/ml (total salt), K1 was present at 50 μg per dose, and MF59 was mixed with the antigens at a 1:1 volume ratio. Antigens were each present at 10 μg in a 100 μL dose for intramuscular injection.

Four or five-week old mice (CD1) were immunized with prime-booster injections with a 14-day interval. Control mice received equal amounts of adjuvants alone. Serum was collected from mice both pre- and post-vaccination to document serum antibody titers to each protein component in the combination vaccine. These titers were measured by Luminex technology using the recombinant vaccine antigens conjugated to microspheres.

Renal Abscess Model:

Immunized animals were challenged on day 24 by intravenous injection of a sublethal dose of S. aureus (~2-6×10$^7$ CFU, where the specific inoculum varied depending on the challenge strain). On day 28, mice were euthanized and kidneys were removed and homogenized in 2 mL of PBS and plated on agar media in duplicate for determination of colony forming units (CFU). Kidneys were also processed for histopathology.

Peritonitis Model:

Separately, immunized animals were challenged on day 24 by intraperitoneal injection of a lethal dose of S. aureus. (~2-5×10$^8$ CFU) and then monitored daily for 14 days.

Skin Infection Model:

Immunized mice were inoculated by subcutaneous injection in the shaved right flank with 2×10$^7$ CFU S. aureus LAC strain (USA300 clone, which is one of the most important clones worldwide and highly associated to community-acquired cutaneous infections). Mass and abscess formation (size and dermonecrosis) were monitored at 24-hour intervals over a course of 7 days. The size of an abscess and associated overlying dermonecrotic lesion was determined using image analysis software. Mouse skin and abscesses were harvested on day 7 post inoculation for CFU enumeration. This model was used only with the Al—H/K1 adjuvant.

Results were as follows:

|   | Adjuvant alone | | | 5-valent | | | 6-valent | | |
|---|---|---|---|---|---|---|---|---|---|
|   | Al—H | Al—H/K1 | MF59 | Al—H | Al—H/K1 | MF59 | Al—H | Al—H/K1 | MF59 |
|   | Renal abscess - log reduction in median cfu/ml | | | | | | | | |
| A | — | — | — | 1.5** | 1.3** | 0.93** | 1.57** | 2.31** | 1.07** |
|   | Peritonitis - % survival | | | | | | | | |
| B | 29 | 42 | 33 | 67* | 88** | 67* | 83** | 92** | 71** |
|   | Skin infection - log reduction in median cfu/ml | | | | | | | | |
| C | N/A | — | — | — | 3.35 | — | — | 4.39 | — |

*p ≤ 0.05 compared to control;
**p < 0.01 compared to control

These results demonstrate that the mutant SpAkR improves the 5-valent Combo-1 product in both models. Furthermore, the best results were seen using the Al—H/K1 adjuvant. Strikingly, results in the renal abscess model the 6-valent vaccine with Al—H/K1 approximated to sterility.

In the peritonitis model, the 6-valent vaccine with Al—H/K1 was statistically superior when compared to the negative control (see table above), and also when compared to the 5-valent Al—H vaccine. In the abscess model, the 6-valent vaccine with Al—H/K1 was statistically superior when compared to the negative control (see table above), to the 5-valent Al—H vaccine, and to the 5-valent Al—H/K1 vaccine, thus showing that the contribution of the mutant SpA goes beyond the enhancement which was due solely to the K1 agonist.

In the skin infection model, the 5-valent and 6-valent vaccines both significantly reduced abscess formation and CFU counts (see table above). Dermonecrosis was absent in the vaccinated mice while it was observed in all mice that received adjuvant alone ('N/A' in table). Furthermore, CFU reduction was significantly improved by the inclusion of SpAkR in the vaccine, and fewer mice were observed with distinguishable abscesses at a macroscopic level (71% vs. 88%).

Anti-SpA titers were also compared for the three adjuvants. Median titers using Al—H or MF59 were not significantly different, but the titer using Al—H/K1 was significantly higher than with Al—H alone (p=0.0047, Mann-Whitney test) and than with MF59 (p=0.01). Thus the formulation which performed best in the functional assays was the one which elicited the highest anti-SpA antibody titres, in line with the hypothesis that SpA's activity as a vaccine antigen depends on antibodies, which can bind it and inhibit its immune-evasion activity.

It will be understood that the invention has been described by way of example only and modifications may be made whilst remaining within the scope and spirit of the invention.

REFERENCES

[1] Sheridan (2009) *Nature Biotechnology* 27:499-501.
[2] Kuklin et al. (2006) *Infect Immun.* 74(4):2215-23.
[3] Fowler et al. (2013) *JAMA* 309(13):1368-78.
[4] WO2010/119343.
[5] WO2013/030378.
[6] Sjodahl (1977) *J. Biochem.* 73:343-351.
[7] Uhlen et al. (1984) *J. Biol. Chem.* 259:1695-1702 & 13628 (Corr.).
[8] WO2007/071692.
[9] Kim et al. (2010) *J Exp Med* 207(9):1863-70.
[10] WO2013/092985.
[11] WO2014/033190.
[12] WO2014/033191.
[13] WO2014/033192.
[14] WO2014/033193.
[15] Sebulsky & Heinrichs (2001) *J Bacteriol* 183:4994-5000.
[16] Sebulsky et al. (2003) *J Biol Chem* 278:49890-900.
[17] Rable & Wardenburg (2009) *Infect Immun* 77:2712-8.
[18] WO2007/145689.
[19] WO2009/029831.
[20] WO2006/110603.
[21] Stranger-Jones et al. (2006) *PNAS USA* 103:16942-7.
[22] Wardenburg et al. (2007) *Infect Immun* 75:1040-4.
[23] Prabhakara et al. (2011) *J Immunol* 186:155.29
[24] Kuroda et al. (2001) *Lancet* 357:1225-1240.
[25] Needleman & Wunsch (1970) *J. Mol. Biol.* 48, 443-453.
[26] Rice et al. (2000) *Trends Genet* 16:276-277.
[27] U.S. Pat. No. 6,355,271.
[28] WO00/23105.
[29] *Vaccine Design* . . . (1995) eds. Powell & Newman. ISBN: 030644867X. Plenum.
[30] WO90/14837.
[31] Garçon et al. (2012) *Expert Rev Vaccines* 11:349-66.
[32] WO90/14837.
[33] Podda & Del Giudice (2003) *Expert Rev Vaccines* 2:197-203.
[34] Podda (2001) *Vaccine* 19: 2673-2680.
[35] *Vaccine Design: The Subunit and Adjuvant Approach* (eds. Powell & Newman) Plenum Press 1995 (ISBN 0-306-44867-X).
[36] *Vaccine Adjuvants: Preparation Methods and Research Protocols* (Volume 42 of *Methods in Molecular Medicine* series). ISBN: 1-59259-083-7. Ed. O'Hagan.
[37] WO2008/043774.
[38] Allison & Byars (1992) *Res Immunol* 143:519-25.
[39] Hariharan et al. (1995) *Cancer Res* 55:3486-9.
[40] US-2007/014805.
[41] US-2007/0191314.
[42] Suli et al. (2004) *Vaccine* 22(25-26):3464-9.
[43] WO95/11700.
[44] U.S. Pat. No. 6,080,725.
[45] WO2005/097181.
[46] WO2006/113373.
[47] U.S. Pat. No. 5,057,540.
[48] WO96/33739.
[49] EP-A-0109942.
[50] WO96/11711.
[51] WO00/07621.
[52] Barr et al. (1998) *Advanced Drug Delivery Reviews* 32:247-271.
[53] Sjolanderet et al. (1998) *Advanced Drug Delivery Reviews* 32:321-338.
[54] EP-A-0689454.
[55] Meraldi et al. (2003) *Vaccine* 21:2485-2491.
[56] Pajak et al. (2003) *Vaccine* 21:836-842.
[57] Kandimalla et al. (2003) *Nucleic Acids Research* 31:2393-2400.
[58] WO02/26757.
[59] WO99/62923.
[60] Krieg (2003) *Nature Medicine* 9:831-835.
[61] McCluskie et al. (2002) *FEMS Immunology and Medical Microbiology* 32:179-185.
[62] WO98/40100.
[63] U.S. Pat. No. 6,207,646.
[64] U.S. Pat. No. 6,239,116.
[65] U.S. Pat. No. 6,429,199.
[66] Kandimalla et al. (2003) *Biochemical Society Transactions* 31 (part 3):654-658.
[67] Blackwell et al. (2003) *J Immunol* 170:4061-4068.
[68] Krieg (2002) *Trends Immunol* 23:64-65.
[69] WO01/95935.
[70] Kandimalla et al. (2003) *BBRC* 306:948-953.
[71] Bhagat et al. (2003) *BBRC* 300:853-861.
[72] WO03/035836.
[73] WO01/22972.
[74] Schellack et al. (2006) *Vaccine* 24:5461-72.
[75] Kamath et al. (2008) *Eur J Immunol* 38:1247-56.
[76] Riedl et al. (2008) *Vaccine* 26:3461-8.
[77] WO95/17211.
[78] WO98/42375.
[79] Beignon et al. (2002) *Infect Immun* 70:3012-3019.
[80] Pizza et al. (2001) *Vaccine* 19:2534-2541.
[81] Pizza et al. (2000) *Int J Med Microbiol* 290:455-461.
[82] Scharton-Kersten et al. (2000) *Infect Immun* 68:5306-5313.
[83] Ryan et al. (1999) *Infect Immun* 67:6270-6280.
[84] Partidos et al. (1999) *Immunol Lett* 67:209-216.
[85] Peppoloni et al. (2003) *Expert Rev Vaccines* 2:285-293.
[86] Pine et al. (2002) *J Control Release* 85:263-270.
[87] Tebbey et al. (2000) *Vaccine* 18:2723-34.
[88] Domenighini et al. (1995) *Mol Microbiol* 15:1165-1167.
[89] Rosenberg et al. (2010) *J Immunol* 184:136.20.
[90] U.S. Pat. No. 4,666,886.
[91] WO2009/118296.
[92] WO2008/005555.
[93] WO2009/111337.
[94] WO2009/067081.
[95] WO2007/040840.
[96] WO2010/014913.
[97] WO2012/031140.
[98] WO2013/132041.
[99] U.S. Pat. No. 4,680,338.
[100] U.S. Pat. No. 4,988,815.

[101] WO92/15582.
[102] Stanley (2002) *Clin Exp Dermatol* 27:571-577.
[103] Wu et al. (2004) *Antiviral Res.* 64(2):79-83.
[104] Vasilakos et al. (2000) *Cell Immunol.* 204(1):64-74.
[105] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[106] Jones (2003) *Curr Opin Investig Drugs* 4:214-218.
[107] Steinhagen et al. (2011) *Vaccine* 29:3341-55.
[108] Myers et al. (1990) pages 145-156 of *Cellular and molecular aspects of endotoxin reactions.*
[109] Ulrich (2000) Chapter 16 (pages 273-282) of reference 36.
[110] Johnson et al. (1999) *J Med Chem* 42:4640-9.
[111] Baldrick et al. (2002) *Regulatory Toxicol Pharmacol* 35:398-413.
[112] Coler et al. (2011) *PLoS ONE* 6(1):e16333.
[113] Johnson et al. (1999) *Bioorg Med Chem Lett* 9:2273-2278.
[114] Evans et al. (2003) *Expert Rev Vaccines* 2:219-229.
[115] Bazin et al. (2006) *Tetrahedron Lett* 47:2087-92.
[116] Wong et al. (2003) *J Clin Pharmacol* 43(7):735-42.
[117] US2005/0215517.
[118] WO03/011223.
[119] WO2011/027222.
[120] WO2013/131985
[121] Gennaro (2000) *Remington: The Science and Practice of Pharmacy.* 20th edition, ISBN: 0683306472.
[122] *Methods In Enzymology* (S. Colowick and N. Kaplan, eds., Academic Press, Inc.)
[123] *Handbook of Experimental Immunology,* Vols. I-IV (D. M. Weir and C. C. Blackwell, eds, 1986, Blackwell Scientific Publications)
[124] Sambrook et al. (2001) *Molecular Cloning: A Laboratory Manual,* 3rd edition (Cold Spring Harbor Laboratory Press).
[125] *Handbook of Surface and Colloidal Chemistry* (Birdi, K. S. ed., CRC Press, 1997)
[126] Ausubel et al. (eds) (2002) *Short protocols in molecular biology,* 5th edition (Current Protocols).
[127] *Molecular Biology Techniques: An Intensive Laboratory Course,* (Ream et al., eds., 1998, Academic Press)
[128] *PCR (Introduction to Biotechniques Series),* 2nd ed. (Newton & Graham eds., 1997, Springer Verlag)
[129] Geysen et al. (1984) *PNAS USA* 81:3998-4002.
[130] Carter (1994) *Methods Mol Biol* 36:207-23.
[131] Jameson, B A et al. 1988, *CABIOS* 4(1):181-186.
[132] Raddrizzani & Hammer (2000) *Brief Bioinform* 1(2):179-89.
[133] Bublil et al. (2007) *Proteins* 68(1):294-304.
[134] De Lalla et al. (1999) *J. Immunol.* 163:1725-29.
[135] Kwok et al. (2001) *Trends Immunol* 22:583-88.
[136] Brusic et al. (1998) *Bioinformatics* 14(2):121-30
[137] Meister et al. (1995) *Vaccine* 13(6):581-91.
[138] Roberts et al. (1996) *AIDS Res Hum Retroviruses* 12(7):593-610.
[139] Maksyutov & Zagrebelnaya (1993) *Comput Appl Biosci* 9(3):291-7.
[140] Feller & de la Cruz (1991) *Nature* 349(6311):720-1.
[141] Hopp (1993) *Peptide Research* 6:183-190.
[142] Welling et al. (1985) *FEBS Lett.* 188:215-218.
[143] Davenport et al. (1995) *Immunogenetics* 42:392-297.
[144] Tsurui & Takahashi (2007) *J Pharmacol Sci.* 105(4):299-316.
[145] Tong et al. (2007) *Brief Bioinform.* 8(2):96-108.
[146] Schirle et al. (2001) *J Immunol Methods.* 257(1-2):1-16.
[147] Chen et al. (2007) *Amino Acids* 33(3):423-8.
[148] *Current Protocols in Molecular Biology* (F. M. Ausubel et al., eds., 1987) Supplement 30
[149] Smith & Waterman (1981) *Adv. Appl. Math.* 2: 482-489.

The invention claimed is:

1. An antigen comprising amino acids 1 to 67 of SEQ ID NO: 49, wherein the dipeptide at positions 60 and 61 of SEQ ID NO:49 is not QQ.

2. The antigen according to claim 1, comprising SEQ ID NO: 49 wherein the dipeptide at positions 60 and 61 of SEQ ID NO:49 is not QQ.

3. An antigen according to claim 1, wherein the antigen elicits antibodies in a mammal that recognise SEQ ID NO: 43 or SEQ ID NO: 54.

4. An antigen according to claim 1 which has decreased affinity, relative to unmodified Staphylococcal protein A (SpA) having SEQ ID NO:43, for the Fcγ portion of human IgG.

5. An antigen according to claim 4 which has decreased affinity, relative to unmodified SpA having SEQ ID NO:43, for the Fab portion of $V_H3$-containing human B cell receptors.

6. An antigen according to claim 1 comprising SEQ ID NO: 43, and wherein at least one amino acid selected from position 43, 44, 70, 71, 96, 97, 104, 105, 131, 132, 162, 163, 189, 190, 220, 221, 247, 248, 278, 279, 305, and 306 of SEQ ID NO: 43 is mutated.

7. An antigen according to claim 1 comprising a sequence selected from SEQ ID NO:51, SEQ ID NO: 52, SEQ ID NO: 47, and SEQ ID NO: 48.

8. A fusion protein comprising an antigen according to claim 1 and another protein.

9. An immunogenic composition comprising an antigen according to claim 1 and one or more pharmaceutical carrier(s) and/or excipient(s).

10. The immunogenic composition according to claim 9, wherein the immunogenic composition also comprises an adjuvant.

11. The immunogenic composition according to claim 10, wherein said adjuvant is selected from the group consisting of:
aluminium salts, particularly aluminium hydroxides and aluminium phosphates;
human TLR agonists, particularly TLR7 agonists; and
a mixture thereof.

12. The immunogenic composition according to claim 10, wherein said adjuvant is a TLR7 agonist compound of the following formula (K):

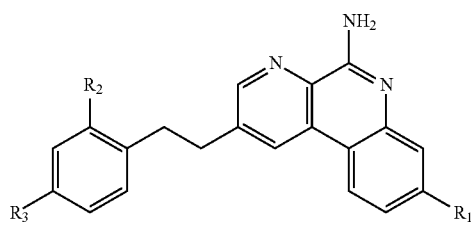

wherein:
$R^1$ is H, $C_1$-$C_6$alkyl, —$C(R^5)_2$OH, -$L^1R^5$, -$L^1R^6$, -$L^2R^5$, -$L^2R^6$, -O$L^2R^5$, or -O$L^2R^6$;
$L^1$ is —C(O)— or —O—;
$L^2$ is $C_1$-$C_6$alkylene, $C_2$-$C_6$alkenylene, arylene, heteroarylene or —(($CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —(($CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, -O$L^3R^5$, -O$L^3R^7$, -O$L^3L^4R^7$, -O$L^3L^4L^3R^7$, —$OR^8$, -O$L^3L^4R^5$, -O$L^3L^4L^3R^5$ and —$C(R^5)_2$OH;
each $R^4$ is independently selected from H and fluoro;
$R^5$ is —P(O)($OR^9)_2$,
$R^6$ is —$CF_2$P(O)($OR^9)_2$ or —C(O)$OR^{10}$;
$R^7$ is —$CF_2$P(O)($OR^9)_2$ or —C(O)$OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and
q is 1, 2, 3 or 4;
particularly 3-(5-amino-2-(2-methyl-4-(2-(2-(2-phosphonoethoxy) ethoxy)ethoxy)phenethyl) benzo [f][1,7] naphthyridin-8-yl)propanoic acid (K1).

13. The immunogenic composition according to claim 11, wherein the adjuvant comprises a human TLR agonist adsorbed to an aluminium salt.

14. A method of treating or preventing *Staphylococcus aureus* disease in a mammal, comprising administering to a mammal in need thereof an immunologically effective amount of the immunogenic composition according to claim 11.

15. The method according to claim 14 where said mammal is a human.

16. The antigen according to claim 1 wherein said dipeptide is KR.

17. The antigen according to claim 2 wherein said dipeptide is KR.

18. The fusion protein according to claim 8, wherein said another protein is selected from the group consisting of EsxA, EsxB, FhuD2, Sta011, and Hla antigens.

19. An immunogenic composition comprising a fusion protein according to claim 8 and one or more pharmaceutical carrier(s) and/or excipient(s).

20. The immunogenic composition according to claim 10, wherein the adjuvant is an oil-in-water emulsion.

21. The immunogenic composition according to claim 10, wherein the adjuvant is a saponin formulation.

22. The immunogenic composition according to claim 10, wherein the adjuvant is a non-toxic derivative of LPS.

* * * * *

SEQUENCE LISTING

<160> NUMBER OF SEQ ID NOS: 54

<210> SEQ ID NO 1
<211> LENGTH: 97
<212> TYPE: PRT
<213> ORGANISM: Staphylococcus aureus

<400> SEQUENCE: 1

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
                20                  25                  30

Thr Arg Ala Gln Gly Glu Ile Ala Ala Asn Trp Glu Gly Gln Ala Phe
            35                  40                  45

Ser Arg Phe Glu Glu Gln Phe Gln Gln Leu Ser Pro Lys Val Glu Lys
        50                  55                  60

Phe Ala Gln Leu Leu Glu Glu Ile Lys Gln Gln Leu Asn Ser Thr Ala
65                  70                  75                  80

Asp Ala Val Gln Glu Gln Asp Gln Gln Leu Ser Asn Asn Phe Gly Leu
                85                  90                  95

Gln

```
<210> SEQ ID NO 2
<211> LENGTH: 104
<212> TYPE: PRT
<213> ORGANISM: Staphylococcus aureus

<400> SEQUENCE: 2

Met Gly Gly Tyr Lys Gly Ile Lys Ala Asp Gly Gly Lys Val Asp Gln
1               5                   10                  15

Ala Lys Gln Leu Ala Ala Lys Thr Ala Lys Asp Ile Glu Ala Cys Gln
            20                  25                  30

Lys Gln Thr Gln Gln Leu Ala Glu Tyr Ile Glu Gly Ser Asp Trp Glu
        35                  40                  45

Gly Gln Phe Ala Asn Lys Val Lys Asp Val Leu Leu Ile Met Ala Lys
    50                  55                  60

Phe Gln Glu Glu Leu Val Gln Pro Met Ala Asp His Gln Lys Ala Ile
65                  70                  75                  80

Asp Asn Leu Ser Gln Asn Leu Ala Lys Tyr Asp Thr Leu Ser Ile Lys
                85                  90                  95

Gln Gly Leu Asp Arg Val Asn Pro
            100

<210> SEQ ID NO 3
<211> LENGTH: 302
<212> TYPE: PRT
<213> ORGANISM: Staphylococcus aureus

<400> SEQUENCE: 3

Met Lys Lys Leu Leu Pro Leu Ile Ile Met Leu Leu Val Leu Ala
1               5                   10                  15

Ala Cys Gly Asn Gln Gly Glu Lys Asn Asn Lys Ala Glu Thr Lys Ser
            20                  25                  30

Tyr Lys Met Asp Asp Gly Lys Thr Val Asp Ile Pro Lys Asp Pro Lys
        35                  40                  45

Arg Ile Ala Val Val Ala Pro Thr Tyr Ala Gly Gly Leu Lys Lys Leu
    50                  55                  60

Gly Ala Asn Ile Val Ala Val Asn Gln Gln Val Asp Gln Ser Lys Val
65                  70                  75                  80

Leu Lys Asp Lys Phe Lys Gly Val Thr Lys Ile Gly Asp Gly Asp Val
                85                  90                  95

Glu Lys Val Ala Lys Glu Lys Pro Asp Leu Ile Ile Val Tyr Ser Thr
            100                 105                 110

Asp Lys Asp Ile Lys Lys Tyr Gln Lys Val Ala Pro Thr Val Val Val
        115                 120                 125

Asp Tyr Asn Lys His Lys Tyr Leu Glu Gln Gln Glu Met Leu Gly Lys
    130                 135                 140

Ile Val Gly Lys Glu Asp Lys Val Lys Ala Trp Lys Lys Asp Trp Glu
145                 150                 155                 160

Glu Thr Thr Ala Lys Asp Gly Lys Glu Ile Lys Ala Ile Gly Gln
                165                 170                 175

Asp Ala Thr Val Ser Leu Phe Asp Glu Phe Asp Lys Lys Leu Tyr Thr
            180                 185                 190

Tyr Gly Asp Asn Trp Gly Arg Gly Gly Glu Val Leu Tyr Gln Ala Phe
        195                 200                 205

Gly Leu Lys Met Gln Pro Glu Gln Gln Lys Leu Thr Ala Lys Ala Gly
    210                 215                 220

Trp Ala Glu Val Lys Gln Glu Glu Ile Glu Lys Tyr Ala Gly Asp Tyr
```

```
                225                 230                 235                 240
Ile Val Ser Thr Ser Glu Gly Lys Pro Thr Pro Gly Tyr Glu Ser Thr
                    245                 250                 255

Asn Met Trp Lys Asn Leu Lys Ala Thr Lys Glu Gly His Ile Val Lys
                260                 265                 270

Val Asp Ala Gly Thr Tyr Trp Tyr Asn Asp Pro Tyr Thr Leu Asp Phe
            275                 280                 285

Met Arg Lys Asp Leu Lys Glu Lys Leu Ile Lys Ala Ala Lys
    290                 295                 300

<210> SEQ ID NO 4
<211> LENGTH: 256
<212> TYPE: PRT
<213> ORGANISM: Staphylococcus aureus

<400> SEQUENCE: 4

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
                20                  25                  30

Val Lys Lys Ser Phe Glu Lys Thr Leu Ser Met Tyr Pro Ile Lys Asn
            35                  40                  45

Leu Glu Asp Leu Tyr Asp Lys Glu Gly Tyr Arg Asp Asp Gln Phe Asp
        50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
                100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
        130                 135                 140

Lys Ile Lys Lys Glu Ile Glu Asn Phe Lys Phe Val Gln Tyr Gly
145                 150                 155                 160

Asp Phe Lys Asn Leu Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 5
<211> LENGTH: 319
<212> TYPE: PRT
<213> ORGANISM: Staphylococcus aureus

<400> SEQUENCE: 5

Met Lys Thr Arg Ile Val Ser Ser Val Thr Thr Thr Leu Leu Leu Gly
```

```
  1               5                  10                 15
Ser Ile Leu Met Asn Pro Val Ala Asn Ala Ala Asp Ser Asp Ile Asn
             20                  25                 30

Ile Lys Thr Gly Thr Thr Asp Ile Gly Ser Asn Thr Thr Val Lys Thr
             35                  40                 45

Gly Asp Leu Val Thr Tyr Asp Lys Glu Asn Gly Met His Lys Lys Val
 50                  55                 60

Phe Tyr Ser Phe Ile Asp Asp Lys Asn His Asn Lys Lys Leu Leu Val
 65                  70                 75                 80

Ile Arg Thr Lys Gly Thr Ile Ala Gly Gln Tyr Arg Val Tyr Ser Glu
                 85                  90                 95

Glu Gly Ala Asn Lys Ser Gly Leu Ala Trp Pro Ser Ala Phe Lys Val
             100                 105                110

Gln Leu Gln Leu Pro Asp Asn Glu Val Ala Gln Ile Ser Asp Tyr Tyr
             115                 120                125

Pro Arg Asn Ser Ile Asp Thr Lys Glu Tyr Met Ser Thr Leu Thr Tyr
             130                 135                140

Gly Phe Asn Gly Asn Val Thr Gly Asp Asp Thr Gly Lys Ile Gly Gly
145                 150                 155                160

Leu Ile Gly Ala Asn Val Ser Ile Gly His Thr Leu Lys Tyr Val Gln
                 165                 170                175

Pro Asp Phe Lys Thr Ile Leu Glu Ser Pro Thr Asp Lys Lys Val Gly
             180                 185                190

Trp Lys Val Ile Phe Asn Asn Met Val Asn Gln Asn Trp Gly Pro Tyr
                 195                 200                205

Asp Arg Asp Ser Trp Asn Pro Val Tyr Gly Asn Gln Leu Phe Met Lys
             210                 215                220

Thr Arg Asn Gly Ser Met Lys Ala Ala Asp Asn Phe Leu Asp Pro Asn
225                 230                 235                240

Lys Ala Ser Ser Leu Leu Ser Ser Gly Phe Ser Pro Asp Phe Ala Thr
                 245                 250                255

Val Ile Thr Met Asp Arg Lys Ala Ser Lys Gln Gln Thr Asn Ile Asp
             260                 265                270

Val Ile Tyr Glu Arg Val Arg Asp Asp Tyr Gln Leu His Trp Thr Ser
             275                 280                285

Thr Asn Trp Lys Gly Thr Asn Thr Lys Asp Lys Trp Ile Asp Arg Ser
             290                 295                300

Ser Glu Arg Tyr Lys Ile Asp Trp Glu Lys Glu Glu Met Thr Asn
305                 310                 315

<210> SEQ ID NO 6
<211> LENGTH: 285
<212> TYPE: PRT
<213> ORGANISM: Staphylococcus aureus

<400> SEQUENCE: 6

Cys Gly Asn Gln Gly Glu Lys Asn Asn Lys Ala Glu Thr Lys Ser Tyr
 1               5                  10                 15

Lys Met Asp Asp Gly Lys Thr Val Asp Ile Pro Lys Asp Pro Lys Arg
             20                  25                 30

Ile Ala Val Val Ala Pro Thr Tyr Ala Gly Gly Leu Lys Lys Leu Gly
             35                  40                 45

Ala Asn Ile Val Ala Val Asn Gln Gln Val Asp Gln Ser Lys Val Leu
 50                  55                 60
```

Lys Asp Lys Phe Lys Gly Val Thr Lys Ile Gly Asp Gly Asp Val Glu
 65                  70                  75                  80

Lys Val Ala Lys Glu Lys Pro Asp Leu Ile Ile Val Tyr Ser Thr Asp
                 85                  90                  95

Lys Asp Ile Lys Lys Tyr Gln Lys Val Ala Pro Thr Val Val Val Asp
            100                 105                 110

Tyr Asn Lys His Lys Tyr Leu Glu Gln Gln Glu Met Leu Gly Lys Ile
        115                 120                 125

Val Gly Lys Glu Asp Lys Val Lys Ala Trp Lys Lys Asp Trp Glu Glu
    130                 135                 140

Thr Thr Ala Lys Asp Gly Lys Glu Ile Lys Lys Ala Ile Gly Gln Asp
145                 150                 155                 160

Ala Thr Val Ser Leu Phe Asp Glu Phe Asp Lys Lys Leu Tyr Thr Tyr
                165                 170                 175

Gly Asp Asn Trp Gly Arg Gly Gly Glu Val Leu Tyr Gln Ala Phe Gly
            180                 185                 190

Leu Lys Met Gln Pro Glu Gln Gln Lys Leu Thr Ala Lys Ala Gly Trp
        195                 200                 205

Ala Glu Val Lys Gln Glu Ile Glu Lys Tyr Ala Gly Asp Tyr Ile
    210                 215                 220

Val Ser Thr Ser Glu Gly Lys Pro Thr Pro Gly Tyr Glu Ser Thr Asn
225                 230                 235                 240

Met Trp Lys Asn Leu Lys Ala Thr Lys Glu Gly His Ile Val Lys Val
                245                 250                 255

Asp Ala Gly Thr Tyr Trp Tyr Asn Asp Pro Tyr Thr Leu Asp Phe Met
            260                 265                 270

Arg Lys Asp Leu Lys Glu Lys Leu Ile Lys Ala Ala Lys
        275                 280                 285

<210> SEQ ID NO 7
<211> LENGTH: 288
<212> TYPE: PRT
<213> ORGANISM: Staphylococcus aureus

<400> SEQUENCE: 7

Met Ala Ser Cys Gly Asn Gln Gly Glu Lys Asn Asn Lys Ala Glu Thr
1               5                   10                  15

Lys Ser Tyr Lys Met Asp Asp Gly Lys Thr Val Asp Ile Pro Lys Asp
            20                  25                  30

Pro Lys Arg Ile Ala Val Val Ala Pro Thr Tyr Ala Gly Gly Leu Lys
        35                  40                  45

Lys Leu Gly Ala Asn Ile Val Ala Val Asn Gln Gln Val Asp Gln Ser
    50                  55                  60

Lys Val Leu Lys Asp Lys Phe Lys Gly Val Thr Lys Ile Gly Asp Gly
65                  70                  75                  80

Asp Val Glu Lys Val Ala Lys Glu Lys Pro Asp Leu Ile Ile Val Tyr
                85                  90                  95

Ser Thr Asp Lys Asp Ile Lys Lys Tyr Gln Lys Val Ala Pro Thr Val
            100                 105                 110

Val Val Asp Tyr Asn Lys His Lys Tyr Leu Glu Gln Gln Glu Met Leu
        115                 120                 125

Gly Lys Ile Val Gly Lys Glu Asp Lys Val Lys Ala Trp Lys Lys Asp
    130                 135                 140

Trp Glu Glu Thr Thr Ala Lys Asp Gly Lys Glu Ile Lys Lys Ala Ile
145                 150                 155                 160

```
Gly Gln Asp Ala Thr Val Ser Leu Phe Asp Glu Phe Asp Lys Lys Leu
            165                 170                 175

Tyr Thr Tyr Gly Asp Asn Trp Gly Arg Gly Gly Glu Val Leu Tyr Gln
            180                 185                 190

Ala Phe Gly Leu Lys Met Gln Pro Glu Gln Lys Leu Thr Ala Lys
            195                 200                 205

Ala Gly Trp Ala Glu Val Lys Gln Glu Glu Ile Glu Lys Tyr Ala Gly
            210                 215                 220

Asp Tyr Ile Val Ser Thr Ser Glu Gly Lys Pro Thr Pro Gly Tyr Glu
225                 230                 235                 240

Ser Thr Asn Met Trp Lys Asn Leu Lys Ala Thr Lys Glu Gly His Ile
            245                 250                 255

Val Lys Val Asp Ala Gly Thr Tyr Trp Tyr Asn Asp Pro Tyr Thr Leu
            260                 265                 270

Asp Phe Met Arg Lys Asp Leu Lys Glu Lys Leu Ile Lys Ala Ala Lys
            275                 280                 285

<210> SEQ ID NO 8
<211> LENGTH: 234
<212> TYPE: PRT
<213> ORGANISM: Staphylococcus aureus

<400> SEQUENCE: 8

Met Gly Cys Gly Ile Gly Lys Glu Ala Glu Val Lys Lys Ser Phe Glu
1               5                   10                  15

Lys Thr Leu Ser Met Tyr Pro Ile Lys Asn Leu Glu Asp Leu Tyr Asp
            20                  25                  30

Lys Glu Gly Tyr Arg Asp Asp Gln Phe Asp Lys Asn Asp Lys Gly Thr
        35                  40                  45

Trp Ile Ile Asn Ser Glu Met Val Ile Gln Pro Asn Asn Glu Asp Met
    50                  55                  60

Val Ala Lys Gly Met Val Leu Tyr Met Asn Arg Asn Thr Lys Thr Thr
65                  70                  75                  80

Asn Gly Tyr Tyr Tyr Val Asp Val Thr Lys Asp Glu Asp Glu Gly Lys
            85                  90                  95

Pro His Asp Asn Glu Lys Arg Tyr Pro Val Lys Met Val Asp Asn Lys
            100                 105                 110

Ile Ile Pro Thr Lys Glu Ile Lys Asp Glu Lys Ile Lys Lys Glu Ile
            115                 120                 125

Glu Asn Phe Lys Phe Phe Val Gln Tyr Gly Asp Phe Lys Asn Leu Lys
            130                 135                 140

Asn Tyr Lys Asp Gly Asp Ile Ser Tyr Asn Pro Glu Val Pro Ser Tyr
145                 150                 155                 160

Ser Ala Lys Tyr Gln Leu Thr Asn Asp Asp Tyr Asn Val Lys Gln Leu
            165                 170                 175

Arg Lys Arg Tyr Asp Ile Pro Thr Ser Lys Ala Pro Lys Leu Leu Leu
            180                 185                 190

Lys Gly Ser Gly Asn Leu Lys Gly Ser Ser Val Gly Tyr Lys Asp Ile
            195                 200                 205

Glu Phe Thr Phe Val Glu Lys Lys Glu Glu Asn Ile Tyr Phe Ser Asp
            210                 215                 220

Ser Leu Asp Tyr Lys Lys Ser Gly Asp Val
225                 230
```

<210> SEQ ID NO 9
<211> LENGTH: 256
<212> TYPE: PRT
<213> ORGANISM: Staphylococcus aureus

<400> SEQUENCE: 9

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

Val Lys Lys Ser Phe Glu Lys Thr Leu Ser Met Tyr Pro Ile Lys Asn
        35                  40                  45

Leu Glu Asp Leu Tyr Asp Lys Glu Gly Tyr Arg Asp Asp Gln Phe Asp
    50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Val Asp Val Thr Lys
            100                 105                 110

Asp Glu Asp Glu Gly Lys Pro His Asp Asn Glu Lys Arg Tyr Pro Val
        115                 120                 125

Lys Met Val Asp Asn Lys Ile Ile Pro Thr Lys Glu Ile Lys Asp Glu
    130                 135                 140

Lys Leu Lys Lys Glu Ile Glu Asn Phe Lys Phe Val Gln Tyr Gly
145                 150                 155                 160

Asp Phe Lys Asn Ile Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu
225                 230                 235                 240

Asn Ile Tyr Phe Ser Asp Ser Leu Asp Tyr Lys Lys Ser Gly Asp Val
                245                 250                 255

<210> SEQ ID NO 10
<211> LENGTH: 256
<212> TYPE: PRT
<213> ORGANISM: Staphylococcus aureus

<400> SEQUENCE: 10

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
            20                  25                  30

Val Lys Lys Ser Phe Glu Lys Thr Leu Ser Met Tyr Pro Ile Lys Asn
        35                  40                  45

Leu Glu Asp Leu Tyr Asp Lys Glu Gly Tyr Arg Asp Asp Gln Phe Asp
    50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn

```
                        85                  90                  95
Arg Asn Thr Lys Thr Thr Asn Gly Tyr Tyr Tyr Val Asp Val Thr Lys
                100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
        130                 135                 140

Lys Val Lys Lys Glu Ile Glu Asn Phe Lys Phe Phe Val Gln Tyr Gly
145                 150                 155                 160

Asp Phe Lys Asn Ile Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205

Ala Pro Lys Leu Leu Lys Gly Ser Gly Asn Leu Lys Gly Ser Ser
210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 11
<211> LENGTH: 256
<212> TYPE: PRT
<213> ORGANISM: Staphylococcus aureus

<400> SEQUENCE: 11

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
                20                  25                  30

Val Lys Lys Ser Phe Glu Lys Thr Leu Ser Met Tyr Pro Ile Lys Asn
            35                  40                  45

Leu Glu Asp Leu Tyr Asp Lys Glu Gly Tyr Arg Asp Asp Gln Phe Asp
        50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
                100                 105                 110

Asp Glu Asp Glu Gly Lys Pro His Asp Asn Glu Lys Arg Tyr Pro Val
            115                 120                 125

Lys Met Val Asp Asn Lys Ile Ile Pro Thr Lys Glu Ile Lys Asp Glu
        130                 135                 140

Lys Leu Lys Lys Glu Ile Glu Asn Phe Lys Phe Phe Val Gln Tyr Gly
145                 150                 155                 160

Asp Phe Lys Asn Val Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
            180                 185                 190

Tyr Asn Val Lys Gln Leu Arg Lys Arg Tyr Asp Ile Pro Thr Ser Lys
        195                 200                 205
```

```
Ala Pro Lys Leu Leu Lys Gly Ser Gly Asn Leu Lys Gly Ser Ser
    210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255
```

<210> SEQ ID NO 12
<211> LENGTH: 293
<212> TYPE: PRT
<213> ORGANISM: Staphylococcus aureus

<400> SEQUENCE: 12

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

<210> SEQ ID NO 13
<211> LENGTH: 293
<212> TYPE: PRT
<213> ORGANISM: Staphylococcus aureus

<400> SEQUENCE: 13

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290

<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic replacement tetramer peptide"

<400> SEQUENCE: 14

Pro Ser Gly Ser
1

<210> SEQ ID NO 15
<211> LENGTH: 258
<212> TYPE: PRT

<213> ORGANISM: Staphylococcus aureus

<400> SEQUENCE: 15

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Pro Ser Gly
            100                 105                 110

Ser Val Gln Pro Asp Phe Lys Thr Ile Leu Glu Ser Pro Thr Asp Lys
        115                 120                 125

Lys Val Gly Trp Lys Val Ile Phe Asn Asn Met Val Asn Gln Asn Trp
    130                 135                 140

Gly Pro Tyr Asp Arg Asp Ser Trp Asn Pro Val Tyr Gly Asn Gln Leu
145                 150                 155                 160

Phe Met Lys Thr Arg Asn Gly Ser Met Lys Ala Ala Asp Asn Phe Leu
                165                 170                 175

Asp Pro Asn Lys Ala Ser Ser Leu Leu Ser Ser Gly Phe Ser Pro Asp
            180                 185                 190

Phe Ala Thr Val Ile Thr Met Asp Arg Lys Ala Ser Lys Gln Gln Thr
        195                 200                 205

Asn Ile Asp Val Ile Tyr Glu Arg Val Arg Asp Asp Tyr Gln Leu His
    210                 215                 220

Trp Thr Ser Thr Asn Trp Lys Gly Thr Asn Thr Lys Asp Lys Trp Ile
225                 230                 235                 240

Asp Arg Ser Ser Glu Arg Tyr Lys Ile Asp Trp Glu Lys Glu Glu Met
                245                 250                 255

Thr Asn

<210> SEQ ID NO 16
<211> LENGTH: 258
<212> TYPE: PRT
<213> ORGANISM: Staphylococcus aureus

<400> SEQUENCE: 16

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Pro Ser Gly
                100                 105                 110

Ser Val Gln Pro Asp Phe Lys Thr Ile Leu Glu Ser Pro Thr Asp Lys
            115                 120                 125

Lys Val Gly Trp Lys Val Ile Phe Asn Asn Met Val Asn Gln Asn Trp
130                 135                 140

Gly Pro Tyr Asp Arg Asp Ser Trp Asn Pro Val Tyr Gly Asn Gln Leu
145                 150                 155                 160

Phe Met Lys Thr Arg Asn Gly Ser Met Lys Ala Ala Asp Asn Phe Leu
                165                 170                 175

Asp Pro Asn Lys Ala Ser Ser Leu Leu Ser Ser Gly Phe Ser Pro Asp
            180                 185                 190

Phe Ala Thr Val Ile Thr Met Asp Arg Lys Ala Ser Lys Gln Gln Thr
        195                 200                 205

Asn Ile Asp Val Ile Tyr Glu Arg Val Arg Asp Asp Tyr Gln Leu His
    210                 215                 220

Trp Thr Ser Thr Asn Trp Lys Gly Thr Asn Thr Lys Asp Lys Trp Ile
225                 230                 235                 240

Asp Arg Ser Ser Glu Arg Tyr Lys Ile Asp Trp Glu Lys Glu Met
                245                 250                 255

Thr Asn

<210> SEQ ID NO 17
<211> LENGTH: 293
<212> TYPE: PRT
<213> ORGANISM: Staphylococcus aureus

<400> SEQUENCE: 17

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Leu Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
    195                 200                 205

-continued

```
Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290

<210> SEQ ID NO 18
<211> LENGTH: 293
<212> TYPE: PRT
<213> ORGANISM: Staphylococcus aureus

<400> SEQUENCE: 18

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Leu Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
```

Glu Glu Met Thr Asn
    290

<210> SEQ ID NO 19
<211> LENGTH: 293
<212> TYPE: PRT
<213> ORGANISM: Staphylococcus aureus

<400> SEQUENCE: 19

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
            85                  90                  95

Gln Ile Ser Asp Leu Tyr Pro Arg Asn Ser Ile Asp Thr Lys Glu Tyr
        100                 105                 110

Met Ser Thr Leu Thr Tyr Gly Phe Asn Gly Asn Val Thr Gly Asp Asp
    115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
        180                 185                 190

Asn Gln Leu Phe Met Lys Thr Arg Asn Gly Ser Met Lys Ala Ala Asp
    195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Ile Asp Arg Ser Ser Glu Arg Tyr Lys Ile Asp Trp Glu Lys
    275                 280                 285

Glu Glu Met Thr Asn
    290

<210> SEQ ID NO 20
<211> LENGTH: 293
<212> TYPE: PRT
<213> ORGANISM: Staphylococcus aureus

<400> SEQUENCE: 20

Ala Asp Ser Asp Ile Asn Ile Lys Thr Gly Thr Thr Asp Ile Gly Ser

```
  1               5                  10                 15
Asn Thr Thr Val Lys Thr Gly Asp Leu Val Thr Tyr Asp Lys Glu Asn
             20                 25                 30
Gly Met Leu Lys Lys Val Phe Tyr Ser Phe Ile Asp Asp Lys Asn His
             35                 40                 45
Asn Lys Lys Leu Leu Val Ile Arg Thr Lys Gly Thr Ile Ala Gly Gln
 50                 55                 60
Tyr Arg Val Tyr Ser Glu Glu Gly Ala Asn Lys Ser Gly Leu Ala Trp
 65                 70                 75                 80
Pro Ser Ala Phe Lys Val Gln Leu Gln Leu Pro Asp Asn Glu Val Ala
             85                 90                 95
Gln Ile Ser Asp Tyr Tyr Pro Arg Asn Ser Ile Asp Thr Lys Glu Tyr
            100                105                110
Met Ser Thr Leu Thr Tyr Gly Phe Asn Gly Asn Val Thr Gly Asp Asp
            115                120                125
Thr Gly Lys Ile Gly Gly Leu Ile Gly Ala Asn Val Ser Ile Gly His
            130                135                140
Thr Leu Lys Tyr Val Gln Pro Leu Phe Lys Thr Ile Leu Glu Ser Pro
145                150                155                160
Thr Asp Lys Lys Val Gly Trp Lys Val Ile Phe Asn Asn Met Val Asn
            165                170                175
Gln Asn Trp Gly Pro Tyr Asp Arg Asp Ser Trp Asn Pro Val Tyr Gly
            180                185                190
Asn Gln Leu Phe Met Lys Thr Arg Asn Gly Ser Met Lys Ala Ala Asp
            195                200                205
Asn Phe Leu Asp Pro Asn Lys Ala Ser Ser Leu Leu Ser Ser Gly Phe
            210                215                220
Ser Pro Asp Phe Ala Thr Val Ile Thr Met Asp Arg Lys Ala Ser Lys
225                230                235                240
Gln Gln Thr Asn Ile Asp Val Ile Tyr Glu Arg Val Arg Asp Asp Tyr
            245                250                255
Gln Leu His Trp Thr Ser Thr Asn Trp Lys Gly Thr Asn Thr Lys Asp
            260                265                270
Lys Trp Ile Asp Arg Ser Ser Glu Arg Tyr Lys Ile Asp Trp Glu Lys
            275                280                285
Glu Glu Met Thr Asn
            290

<210> SEQ ID NO 21
<211> LENGTH: 50
<212> TYPE: PRT
<213> ORGANISM: Staphylococcus aureus

<400> SEQUENCE: 21

Ala Asp Ser Asp Ile Asn Ile Lys Thr Gly Thr Thr Asp Ile Gly Ser
 1               5                  10                 15
Asn Thr Thr Val Lys Thr Gly Asp Leu Val Thr Tyr Asp Lys Glu Asn
             20                 25                 30
Gly Met His Lys Lys Val Phe Tyr Ser Phe Ile Asp Asp Lys Asn His
             35                 40                 45
Asn Lys
 50

<210> SEQ ID NO 22
<211> LENGTH: 63
```

```
<212> TYPE: PRT
<213> ORGANISM: Staphylococcus aureus

<400> SEQUENCE: 22

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly
        50                  55                  60

<210> SEQ ID NO 23
<211> LENGTH: 53
<212> TYPE: PRT
<213> ORGANISM: Staphylococcus aureus

<400> SEQUENCE: 23

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu
        50

<210> SEQ ID NO 24
<211> LENGTH: 50
<212> TYPE: PRT
<213> ORGANISM: Staphylococcus aureus

<400> SEQUENCE: 24

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys
    50

<210> SEQ ID NO 25
<211> LENGTH: 63
<212> TYPE: PRT
<213> ORGANISM: Staphylococcus aureus

<400> SEQUENCE: 25

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly
        50                  55                  60

<210> SEQ ID NO 26
```

```
<211> LENGTH: 53
<212> TYPE: PRT
<213> ORGANISM: Staphylococcus aureus

<400> SEQUENCE: 26

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu
        50

<210> SEQ ID NO 27
<211> LENGTH: 296
<212> TYPE: PRT
<213> ORGANISM: Staphylococcus aureus

<400> SEQUENCE: 27

Met Ala Ser Ala Asp Ser Asp Ile Asn Ile Lys Thr Gly Thr Thr Asp
1               5                   10                  15

Ile Gly Ser Asn Thr Thr Val Lys Thr Gly Asp Leu Val Thr Tyr Asp
                20                  25                  30

Lys Glu Asn Gly Met Leu Lys Lys Val Phe Tyr Ser Phe Ile Asp Asp
            35                  40                  45

Lys Asn His Asn Lys Lys Leu Leu Val Ile Arg Thr Lys Gly Thr Ile
50                  55                  60

Ala Gly Gln Tyr Arg Val Tyr Ser Glu Glu Gly Ala Asn Lys Ser Gly
65                  70                  75                  80

Leu Ala Trp Pro Ser Ala Phe Lys Val Gln Leu Gln Leu Pro Asp Asn
                85                  90                  95

Glu Val Ala Gln Ile Ser Asp Tyr Tyr Pro Arg Asn Ser Ile Asp Thr
            100                 105                 110

Lys Glu Tyr Met Ser Thr Leu Thr Tyr Gly Phe Asn Gly Asn Val Thr
        115                 120                 125

Gly Asp Asp Thr Gly Lys Ile Gly Gly Leu Ile Gly Ala Asn Val Ser
130                 135                 140

Ile Gly His Thr Leu Lys Tyr Val Gln Pro Asp Phe Lys Thr Ile Leu
145                 150                 155                 160

Glu Ser Pro Thr Asp Lys Lys Val Gly Trp Lys Val Ile Phe Asn Asn
                165                 170                 175

Met Val Asn Gln Asn Trp Gly Pro Tyr Asp Arg Asp Ser Trp Asn Pro
            180                 185                 190

Val Tyr Gly Asn Gln Leu Phe Met Lys Thr Arg Asn Gly Ser Met Lys
        195                 200                 205

Ala Ala Asp Asn Phe Leu Asp Pro Asn Lys Ala Ser Ser Leu Leu Ser
    210                 215                 220

Ser Gly Phe Ser Pro Asp Phe Ala Thr Val Ile Thr Met Asp Arg Lys
225                 230                 235                 240

Ala Ser Lys Gln Gln Thr Asn Ile Asp Val Ile Tyr Glu Arg Val Arg
                245                 250                 255

Asp Asp Tyr Gln Leu His Trp Thr Ser Thr Asn Trp Lys Gly Thr Asn
            260                 265                 270

Thr Lys Asp Lys Trp Ile Asp Arg Ser Ser Glu Arg Tyr Lys Ile Asp
        275                 280                 285
```

Trp Glu Lys Glu Glu Met Thr Asn
    290                 295

<210> SEQ ID NO 28
<211> LENGTH: 207
<212> TYPE: PRT
<213> ORGANISM: Staphylococcus aureus

<400> SEQUENCE: 28

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45

Ser Arg Phe Glu Glu Gln Phe Gln Gln Leu Ser Pro Lys Val Glu Lys
    50                  55                  60

Phe Ala Gln Leu Leu Glu Glu Ile Lys Gln Gln Leu Asn Ser Thr Ala
65                  70                  75                  80

Asp Ala Val Gln Glu Gln Asp Gln Gln Leu Ser Asn Asn Phe Gly Leu
                85                  90                  95

Gln Ala Ser Gly Gly Gly Ser Met Gly Gly Tyr Lys Gly Ile Lys Ala
            100                 105                 110

Asp Gly Gly Lys Val Asp Gln Ala Lys Gln Leu Ala Ala Lys Thr Ala
        115                 120                 125

Lys Asp Ile Glu Ala Cys Gln Lys Gln Thr Gln Gln Leu Ala Glu Tyr
    130                 135                 140

Ile Glu Gly Ser Asp Trp Glu Gly Gln Phe Ala Asn Lys Val Lys Asp
145                 150                 155                 160

Val Leu Leu Ile Met Ala Lys Phe Gln Glu Glu Leu Val Gln Pro Met
                165                 170                 175

Ala Asp His Gln Lys Ala Ile Asp Asn Leu Ser Gln Asn Leu Ala Lys
            180                 185                 190

Tyr Asp Thr Leu Ser Ile Lys Gln Gly Leu Asp Arg Val Asn Pro
        195                 200                 205

<210> SEQ ID NO 29
<211> LENGTH: 207
<212> TYPE: PRT
<213> ORGANISM: Staphylococcus aureus

<400> SEQUENCE: 29

Met Gly Gly Tyr Lys Gly Ile Lys Ala Asp Gly Gly Lys Val Asp Gln
1               5                   10                  15

Ala Lys Gln Leu Ala Ala Lys Thr Ala Lys Asp Ile Glu Ala Cys Gln
            20                  25                  30

Lys Gln Thr Gln Gln Leu Ala Glu Tyr Ile Glu Gly Ser Asp Trp Glu
        35                  40                  45

Gly Gln Phe Ala Asn Lys Val Lys Asp Val Leu Leu Ile Met Ala Lys
    50                  55                  60

Phe Gln Glu Glu Leu Val Gln Pro Met Ala Asp His Gln Lys Ala Ile
65                  70                  75                  80

Asp Asn Leu Ser Gln Asn Leu Ala Lys Tyr Asp Thr Leu Ser Ile Lys
                85                  90                  95

Gln Gly Leu Asp Arg Val Asn Pro Ala Ser Gly Gly Gly Ser Met Ala
            100                 105                 110

```
Met Ile Lys Met Ser Pro Glu Glu Ile Arg Ala Lys Ser Gln Ser Tyr
        115                 120                 125

Gly Gln Gly Ser Asp Gln Ile Arg Gln Ile Leu Ser Asp Leu Thr Arg
        130                 135                 140

Ala Gln Gly Glu Ile Ala Ala Asn Trp Glu Gly Gln Ala Phe Ser Arg
145                 150                 155                 160

Phe Glu Glu Gln Phe Gln Gln Leu Ser Pro Lys Val Glu Lys Phe Ala
                165                 170                 175

Gln Leu Leu Glu Glu Ile Lys Gln Gln Leu Asn Ser Thr Ala Asp Ala
            180                 185                 190

Val Gln Glu Gln Asp Gln Gln Leu Ser Asn Asn Phe Gly Leu Gln
        195                 200                 205

<210> SEQ ID NO 30
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic linker peptide"

<400> SEQUENCE: 30

Ala Ser Gly Gly Gly Ser
1               5

<210> SEQ ID NO 31
<211> LENGTH: 205
<212> TYPE: PRT
<213> ORGANISM: Staphylococcus aureus

<400> SEQUENCE: 31

Ala Met Ile Lys Met Ser Pro Glu Glu Ile Arg Ala Lys Ser Gln Ser
1               5                   10                  15

Tyr Gly Gln Gly Ser Asp Gln Ile Arg Gln Ile Leu Ser Asp Leu Thr
            20                  25                  30

Arg Ala Gln Gly Glu Ile Ala Ala Asn Trp Glu Gly Gln Ala Phe Ser
        35                  40                  45

Arg Phe Glu Glu Gln Phe Gln Gln Leu Ser Pro Lys Val Glu Lys Phe
    50                  55                  60

Ala Gln Leu Leu Glu Glu Ile Lys Gln Gln Leu Asn Ser Thr Ala Asp
65                  70                  75                  80

Ala Val Gln Glu Gln Asp Gln Gln Leu Ser Asn Asn Phe Gly Leu Gln
                85                  90                  95

Ala Ser Gly Gly Gly Ser Gly Gly Tyr Lys Gly Ile Lys Ala Asp Gly
            100                 105                 110

Gly Lys Val Asp Gln Ala Lys Gln Leu Ala Ala Lys Thr Ala Lys Asp
        115                 120                 125

Ile Glu Ala Cys Gln Lys Gln Thr Gln Gln Leu Ala Glu Tyr Ile Glu
    130                 135                 140

Gly Ser Asp Trp Glu Gly Gln Phe Ala Asn Lys Val Lys Asp Val Leu
145                 150                 155                 160

Leu Ile Met Ala Lys Phe Gln Glu Glu Leu Val Gln Pro Met Ala Asp
                165                 170                 175

His Gln Lys Ala Ile Asp Asn Leu Ser Gln Asn Leu Ala Lys Tyr Asp
            180                 185                 190

Thr Leu Ser Ile Lys Gln Gly Leu Asp Arg Val Asn Pro
```

195                 200                 205

<210> SEQ ID NO 32
<211> LENGTH: 206
<212> TYPE: PRT
<213> ORGANISM: Staphylococcus aureus

<400> SEQUENCE: 32

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45

Ser Arg Phe Glu Glu Gln Phe Gln Gln Leu Ser Pro Lys Val Glu Lys
    50                  55                  60

Phe Ala Gln Leu Leu Glu Glu Ile Lys Gln Gln Leu Asn Ser Thr Ala
65                  70                  75                  80

Asp Ala Val Gln Glu Gln Asp Gln Gln Leu Ser Asn Asn Phe Gly Leu
                85                  90                  95

Gln Ala Ser Gly Gly Ser Gly Gly Tyr Lys Gly Ile Lys Ala Asp
            100                 105                 110

Gly Gly Lys Val Asp Gln Ala Lys Gln Leu Ala Ala Lys Thr Ala Lys
        115                 120                 125

Asp Ile Glu Ala Cys Gln Lys Gln Thr Gln Gln Leu Ala Glu Tyr Ile
    130                 135                 140

Glu Gly Ser Asp Trp Glu Gly Gln Phe Ala Asn Lys Val Lys Asp Val
145                 150                 155                 160

Leu Leu Ile Met Ala Lys Phe Gln Glu Glu Leu Val Gln Pro Met Ala
                165                 170                 175

Asp His Gln Lys Ala Ile Asp Asn Leu Ser Gln Asn Leu Ala Lys Tyr
            180                 185                 190

Asp Thr Leu Ser Ile Lys Gln Gly Leu Asp Arg Val Asn Pro
        195                 200                 205

<210> SEQ ID NO 33
<211> LENGTH: 233
<212> TYPE: PRT
<213> ORGANISM: Staphylococcus aureus

<400> SEQUENCE: 33

Gly Cys Gly Ile Gly Lys Glu Ala Glu Val Lys Lys Ser Phe Glu Lys
1               5                   10                  15

Thr Leu Ser Met Tyr Pro Ile Lys Asn Leu Glu Asp Leu Tyr Asp Lys
            20                  25                  30

Glu Gly Tyr Arg Asp Asp Gln Phe Asp Lys Asn Asp Lys Gly Thr Trp
        35                  40                  45

Ile Ile Asn Ser Glu Met Val Ile Gln Pro Asn Asn Glu Asp Met Val
    50                  55                  60

Ala Lys Gly Met Val Leu Tyr Met Asn Arg Asn Thr Lys Thr Thr Asn
65                  70                  75                  80

Gly Tyr Tyr Tyr Val Asp Val Thr Lys Asp Glu Asp Glu Gly Lys Pro
                85                  90                  95

His Asp Asn Glu Lys Arg Tyr Pro Val Lys Met Val Asp Asn Lys Ile
            100                 105                 110

Ile Pro Thr Lys Glu Ile Lys Asp Glu Lys Ile Lys Lys Glu Ile Glu

```
            115                 120                 125
Asn Phe Lys Phe Phe Val Gln Tyr Gly Asp Phe Lys Asn Leu Lys Asn
    130                 135                 140

Tyr Lys Asp Gly Asp Ile Ser Tyr Asn Pro Glu Val Pro Ser Tyr Ser
145                 150                 155                 160

Ala Lys Tyr Gln Leu Thr Asn Asp Asp Tyr Asn Val Lys Gln Leu Arg
                165                 170                 175

Lys Arg Tyr Asp Ile Pro Thr Ser Lys Ala Pro Lys Leu Leu Leu Lys
            180                 185                 190

Gly Ser Gly Asn Leu Lys Gly Ser Ser Val Gly Tyr Lys Asp Ile Glu
        195                 200                 205

Phe Thr Phe Val Glu Lys Glu Glu Asn Ile Tyr Phe Ser Asp Ser
210                 215                 220

Leu Asp Tyr Lys Lys Ser Gly Asp Val
225                 230

<210> SEQ ID NO 34
<211> LENGTH: 284
<212> TYPE: PRT
<213> ORGANISM: Staphylococcus aureus

<400> SEQUENCE: 34

Gly Asn Gln Gly Glu Lys Asn Asn Lys Ala Glu Thr Lys Ser Tyr Lys
1               5                   10                  15

Met Asp Asp Gly Lys Thr Val Asp Ile Pro Lys Asp Pro Lys Arg Ile
            20                  25                  30

Ala Val Val Ala Pro Thr Tyr Ala Gly Gly Leu Lys Lys Leu Gly Ala
        35                  40                  45

Asn Ile Val Ala Val Asn Gln Gln Val Asp Gln Ser Lys Val Leu Lys
    50                  55                  60

Asp Lys Phe Lys Gly Val Thr Lys Ile Gly Asp Gly Asp Val Glu Lys
65                  70                  75                  80

Val Ala Lys Glu Lys Pro Asp Leu Ile Ile Val Tyr Ser Thr Asp Lys
                85                  90                  95

Asp Ile Lys Lys Tyr Gln Lys Val Ala Pro Thr Val Val Asp Tyr
            100                 105                 110

Asn Lys His Lys Tyr Leu Glu Gln Gln Glu Met Leu Gly Lys Ile Val
        115                 120                 125

Gly Lys Glu Asp Lys Val Lys Ala Trp Lys Lys Asp Trp Glu Glu Thr
    130                 135                 140

Thr Ala Lys Asp Gly Lys Glu Ile Lys Lys Ala Ile Gly Gln Asp Ala
145                 150                 155                 160

Thr Val Ser Leu Phe Asp Glu Phe Asp Lys Lys Leu Tyr Thr Tyr Gly
                165                 170                 175

Asp Asn Trp Gly Arg Gly Gly Glu Val Leu Tyr Gln Ala Phe Gly Leu
            180                 185                 190

Lys Met Gln Pro Glu Gln Gln Lys Leu Thr Ala Lys Ala Gly Trp Ala
        195                 200                 205

Glu Val Lys Gln Glu Glu Ile Glu Lys Tyr Ala Gly Asp Tyr Ile Val
    210                 215                 220

Ser Thr Ser Glu Gly Lys Pro Thr Pro Gly Tyr Glu Ser Thr Asn Met
225                 230                 235                 240

Trp Lys Asn Leu Lys Ala Thr Lys Glu Gly His Ile Val Lys Val Asp
                245                 250                 255
```

Ala Gly Thr Tyr Trp Tyr Asn Asp Pro Tyr Thr Leu Asp Phe Met Arg
           260                 265                 270

Lys Asp Leu Lys Glu Lys Leu Ile Lys Ala Ala Lys
        275                 280

<210> SEQ ID NO 35
<211> LENGTH: 103
<212> TYPE: PRT
<213> ORGANISM: Staphylococcus aureus
<220> FEATURE:
<221> NAME/KEY: MOD_RES
<222> LOCATION: (30)..(30)
<223> OTHER INFORMATION: Any amino acid which lacks a free thiol or
      absent

<400> SEQUENCE: 35

Gly Gly Tyr Lys Gly Ile Lys Ala Asp Gly Gly Lys Val Asp Gln Ala
1               5                   10                  15

Lys Gln Leu Ala Ala Lys Thr Ala Lys Asp Ile Glu Ala Xaa Gln Lys
            20                  25                  30

Gln Thr Gln Gln Leu Ala Glu Tyr Ile Glu Gly Ser Asp Trp Glu Gly
        35                  40                  45

Gln Phe Ala Asn Lys Val Lys Asp Val Leu Leu Ile Met Ala Lys Phe
    50                  55                  60

Gln Glu Glu Leu Val Gln Pro Met Ala Asp His Gln Lys Ala Ile Asp
65                  70                  75                  80

Asn Leu Ser Gln Asn Leu Ala Lys Tyr Asp Thr Leu Ser Ile Lys Gln
                85                  90                  95

Gly Leu Asp Arg Val Asn Pro
            100

<210> SEQ ID NO 36
<211> LENGTH: 231
<212> TYPE: PRT
<213> ORGANISM: Staphylococcus aureus

<400> SEQUENCE: 36

Gly Ile Gly Lys Glu Ala Glu Val Lys Lys Ser Phe Glu Lys Thr Leu
1               5                   10                  15

Ser Met Tyr Pro Ile Lys Asn Leu Glu Asp Leu Tyr Asp Lys Glu Gly
            20                  25                  30

Tyr Arg Asp Asp Gln Phe Asp Lys Asn Asp Lys Gly Thr Trp Ile Ile
        35                  40                  45

Asn Ser Glu Met Val Ile Gln Pro Asn Asn Glu Asp Met Val Ala Lys
    50                  55                  60

Gly Met Val Leu Tyr Met Asn Arg Asn Thr Lys Thr Thr Asn Gly Tyr
65                  70                  75                  80

Tyr Tyr Val Asp Val Thr Lys Asp Glu Asp Glu Gly Lys Pro His Asp
                85                  90                  95

Asn Glu Lys Arg Tyr Pro Val Lys Met Val Asp Asn Lys Ile Ile Pro
            100                 105                 110

Thr Lys Glu Ile Lys Asp Glu Lys Ile Lys Lys Glu Ile Glu Asn Phe
        115                 120                 125

Lys Phe Phe Val Gln Tyr Gly Asp Phe Lys Asn Leu Lys Asn Tyr Lys
    130                 135                 140

Asp Gly Asp Ile Ser Tyr Asn Pro Glu Val Pro Ser Tyr Ser Ala Lys
145                 150                 155                 160

Tyr Gln Leu Thr Asn Asp Asp Tyr Asn Val Lys Gln Leu Arg Lys Arg

```
                    165                 170                 175

Tyr Asp Ile Pro Thr Ser Lys Ala Pro Lys Leu Leu Lys Gly Ser
            180                 185                 190

Gly Asn Leu Lys Gly Ser Ser Val Gly Tyr Lys Asp Ile Glu Phe Thr
            195                 200                 205

Phe Val Glu Lys Lys Glu Glu Asn Ile Tyr Phe Ser Asp Ser Leu Asp
            210                 215                 220

Tyr Lys Lys Ser Gly Asp Val
225                 230

<210> SEQ ID NO 37
<211> LENGTH: 287
<212> TYPE: PRT
<213> ORGANISM: Staphylococcus aureus

<400> SEQUENCE: 37

Met Ala Ser Gly Asn Gln Gly Glu Lys Asn Lys Ala Glu Thr Lys
1               5                   10                  15

Ser Tyr Lys Met Asp Asp Gly Lys Thr Val Asp Ile Pro Lys Asp Pro
            20                  25                  30

Lys Arg Ile Ala Val Val Ala Pro Thr Tyr Ala Gly Gly Leu Lys Lys
            35                  40                  45

Leu Gly Ala Asn Ile Val Ala Val Asn Gln Gln Val Asp Gln Ser Lys
50                  55                  60

Val Leu Lys Asp Lys Phe Lys Gly Val Thr Lys Ile Gly Asp Gly Asp
65                  70                  75                  80

Val Glu Lys Val Ala Lys Glu Lys Pro Asp Leu Ile Ile Val Tyr Ser
            85                  90                  95

Thr Asp Lys Asp Ile Lys Lys Tyr Gln Lys Val Ala Pro Thr Val Val
            100                 105                 110

Val Asp Tyr Asn Lys His Lys Tyr Leu Glu Gln Gln Glu Met Leu Gly
            115                 120                 125

Lys Ile Val Gly Lys Glu Asp Lys Val Lys Ala Trp Lys Lys Asp Trp
130                 135                 140

Glu Glu Thr Thr Ala Lys Asp Gly Lys Glu Ile Lys Lys Ala Ile Gly
145                 150                 155                 160

Gln Asp Ala Thr Val Ser Leu Phe Asp Glu Phe Asp Lys Lys Leu Tyr
            165                 170                 175

Thr Tyr Gly Asp Asn Trp Gly Arg Gly Gly Glu Val Leu Tyr Gln Ala
            180                 185                 190

Phe Gly Leu Lys Met Gln Pro Glu Gln Gln Lys Leu Thr Ala Lys Ala
            195                 200                 205

Gly Trp Ala Glu Val Lys Gln Glu Glu Ile Glu Lys Tyr Ala Gly Asp
            210                 215                 220

Tyr Ile Val Ser Thr Ser Glu Gly Lys Pro Thr Pro Gly Tyr Glu Ser
225                 230                 235                 240

Thr Asn Met Trp Lys Asn Leu Lys Ala Thr Lys Glu Gly His Ile Val
            245                 250                 255

Lys Val Asp Ala Gly Thr Tyr Trp Tyr Asn Asp Pro Tyr Thr Leu Asp
            260                 265                 270

Phe Met Arg Lys Asp Leu Lys Glu Lys Leu Ile Lys Ala Ala Lys
            275                 280                 285

<210> SEQ ID NO 38
<211> LENGTH: 206
```

<212> TYPE: PRT
<213> ORGANISM: Staphylococcus aureus

<400> SEQUENCE: 38

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45

Ser Arg Phe Glu Glu Gln Phe Gln Gln Leu Ser Pro Lys Val Glu Lys
    50                  55                  60

Phe Ala Gln Leu Leu Glu Glu Ile Lys Gln Gln Leu Asn Ser Thr Ala
65                  70                  75                  80

Asp Ala Val Gln Glu Gln Asp Gln Leu Ser Asn Asn Phe Gly Leu
                85                  90                  95

Gln Ala Ser Gly Gly Gly Ser Gly Gly Tyr Lys Gly Ile Lys Ala Asp
            100                 105                 110

Gly Gly Lys Val Asp Gln Ala Lys Gln Leu Ala Ala Lys Thr Ala Lys
        115                 120                 125

Asp Ile Glu Ala Ala Gln Lys Gln Thr Gln Gln Leu Ala Glu Tyr Ile
    130                 135                 140

Glu Gly Ser Asp Trp Glu Gly Gln Phe Ala Asn Lys Val Lys Asp Val
145                 150                 155                 160

Leu Leu Ile Met Ala Lys Phe Gln Glu Glu Leu Val Gln Pro Met Ala
                165                 170                 175

Asp His Gln Lys Ala Ile Asp Asn Leu Ser Gln Asn Leu Ala Lys Tyr
            180                 185                 190

Asp Thr Leu Ser Ile Lys Gln Gly Leu Asp Arg Val Asn Pro
        195                 200                 205

<210> SEQ ID NO 39
<211> LENGTH: 234
<212> TYPE: PRT
<213> ORGANISM: Staphylococcus aureus

<400> SEQUENCE: 39

Met Gly Ser Gly Ile Gly Lys Glu Ala Glu Val Lys Lys Ser Phe Glu
1               5                   10                  15

Lys Thr Leu Ser Met Tyr Pro Ile Lys Asn Leu Glu Asp Leu Tyr Asp
            20                  25                  30

Lys Glu Gly Tyr Arg Asp Asp Gln Phe Asp Lys Asn Asp Lys Gly Thr
        35                  40                  45

Trp Ile Ile Asn Ser Glu Met Val Ile Gln Pro Asn Asn Glu Asp Met
    50                  55                  60

Val Ala Lys Gly Met Val Leu Tyr Met Asn Arg Asn Thr Lys Thr Thr
65                  70                  75                  80

Asn Gly Tyr Tyr Tyr Val Asp Val Thr Lys Glu Asp Glu Gly Lys
            85                  90                  95

Pro His Asp Asn Glu Lys Arg Tyr Pro Val Lys Met Val Asp Asn Lys
            100                 105                 110

Ile Ile Pro Thr Lys Glu Ile Lys Asp Glu Lys Ile Lys Lys Glu Ile
        115                 120                 125

Glu Asn Phe Lys Phe Phe Val Gln Tyr Gly Asp Phe Lys Asn Leu Lys
    130                 135                 140

```
Asn Tyr Lys Asp Gly Asp Ile Ser Tyr Asn Pro Glu Val Pro Ser Tyr
145                 150                 155                 160

Ser Ala Lys Tyr Gln Leu Thr Asn Asp Asp Tyr Asn Val Lys Gln Leu
                165                 170                 175

Arg Lys Arg Tyr Asp Ile Pro Thr Ser Lys Ala Pro Lys Leu Leu Leu
            180                 185                 190

Lys Gly Ser Gly Asn Leu Lys Gly Ser Ser Val Gly Tyr Lys Asp Ile
        195                 200                 205

Glu Phe Thr Phe Val Glu Lys Glu Glu Asn Ile Tyr Phe Ser Asp
    210                 215                 220

Ser Leu Asp Tyr Lys Lys Ser Gly Asp Val
225                 230
```

<210> SEQ ID NO 40
<211> LENGTH: 205
<212> TYPE: PRT
<213> ORGANISM: Staphylococcus aureus
<220> FEATURE:
<221> NAME/KEY: MOD_RES
<222> LOCATION: (132)..(132)
<223> OTHER INFORMATION: Any amino acid which lacks a free thiol or
      absent

<400> SEQUENCE: 40

```
Ala Met Ile Lys Met Ser Pro Glu Ile Arg Ala Lys Ser Gln Ser
1               5                   10                  15

Tyr Gly Gln Gly Ser Asp Gln Ile Arg Gln Ile Leu Ser Asp Leu Thr
                20                  25                  30

Arg Ala Gln Gly Glu Ile Ala Ala Asn Trp Glu Gly Gln Ala Phe Ser
            35                  40                  45

Arg Phe Glu Glu Gln Phe Gln Gln Leu Ser Pro Lys Val Glu Lys Phe
50                  55                  60

Ala Gln Leu Leu Glu Glu Ile Lys Gln Leu Asn Ser Thr Ala Asp
65                  70                  75                  80

Ala Val Gln Glu Gln Asp Gln Leu Ser Asn Asn Phe Gly Leu Gln
                85                  90                  95

Ala Ser Gly Gly Ser Gly Gly Tyr Lys Gly Ile Lys Ala Asp Gly
            100                 105                 110

Gly Lys Val Asp Gln Ala Lys Gln Leu Ala Ala Lys Thr Ala Lys Asp
        115                 120                 125

Ile Glu Ala Xaa Gln Lys Gln Thr Gln Gln Leu Ala Glu Tyr Ile Glu
        130                 135                 140

Gly Ser Asp Trp Glu Gly Gln Phe Ala Asn Lys Val Lys Asp Val Leu
145                 150                 155                 160

Leu Ile Met Ala Lys Phe Gln Glu Glu Leu Val Gln Pro Met Ala Asp
                165                 170                 175

His Gln Lys Ala Ile Asp Asn Leu Ser Gln Asn Leu Ala Lys Tyr Asp
            180                 185                 190

Thr Leu Ser Ile Lys Gln Gly Leu Asp Arg Val Asn Pro
        195                 200                 205
```

<210> SEQ ID NO 41
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic immunostimulatory oligonucleotide"

```
<220> FEATURE:
<221> NAME/KEY: modified_base
<222> LOCATION: (1)..(1)
<223> OTHER INFORMATION: Inosine
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (11)..(11)
<223> OTHER INFORMATION: Inosine
<220> FEATURE:
<221> NAME/KEY: modified_base
<222> LOCATION: (13)..(13)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (17)..(17)
<223> OTHER INFORMATION: Inosine
<220> FEATURE:
<221> NAME/KEY: modified_base
<222> LOCATION: (19)..(19)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (23)..(23)
<223> OTHER INFORMATION: Inosine
<220> FEATURE:
<221> NAME/KEY: modified_base
<222> LOCATION: (25)..(25)
<223> OTHER INFORMATION: Inosine

<400> SEQUENCE: 41 ncncncnc ncncncncnc ncncnc                                        26

<210> SEQ ID NO 42
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic cationic oligopeptide"

<400> SEQUENCE: 42

Lys Leu Lys Leu Leu Leu Leu Leu Lys Leu Lys
1               5                   10

<210> SEQ ID NO 43
<211> LENGTH: 516
<212> TYPE: PRT
<213> ORGANISM: Staphylococcus aureus

<400> SEQUENCE: 43
```

```
Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
        50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
        355                 360                 365

Glu Asp Gly Asn Lys Pro Gly Lys Glu Asp Asn Lys Lys Pro Gly Lys
    370                 375                 380

Glu Asp Gly Asn Lys Pro Gly Lys Glu Asp Asn Lys Lys Pro Gly Lys
385                 390                 395                 400

Glu Asp Gly Asn Lys Pro Gly Lys Glu Asp Gly Asn Lys Pro Gly Lys
                405                 410                 415
```

```
Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
        435                 440                 445

Asn Lys Leu Ala Asp Lys Asn Met Ile Lys Pro Gly Gln Glu Leu Val
    450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
                485                 490                 495

Phe Gly Gly Leu Ser Leu Ala Leu Gly Ala Ala Leu Leu Ala Gly Arg
            500                 505                 510

Arg Arg Glu Leu
        515

<210> SEQ ID NO 44
<211> LENGTH: 291
<212> TYPE: PRT
<213> ORGANISM: Staphylococcus aureus
<220> FEATURE:
<221> NAME/KEY: MOD_RES
<222> LOCATION: (7)..(8)
<223> OTHER INFORMATION: Any amino acid except Gln
<220> FEATURE:
<221> NAME/KEY: MOD_RES
<222> LOCATION: (34)..(35)
<223> OTHER INFORMATION: Any amino acid except Asp
<220> FEATURE:
<221> NAME/KEY: MOD_RES
<222> LOCATION: (68)..(69)
<223> OTHER INFORMATION: Any amino acid except Gln
<220> FEATURE:
<221> NAME/KEY: MOD_RES
<222> LOCATION: (95)..(96)
<223> OTHER INFORMATION: Any amino acid except Asp
<220> FEATURE:
<221> NAME/KEY: MOD_RES
<222> LOCATION: (126)..(127)
<223> OTHER INFORMATION: Any amino acid except Gln
<220> FEATURE:
<221> NAME/KEY: MOD_RES
<222> LOCATION: (153)..(154)
<223> OTHER INFORMATION: Any amino acid except Asp
<220> FEATURE:
<221> NAME/KEY: MOD_RES
<222> LOCATION: (184)..(185)
<223> OTHER INFORMATION: Any amino acid except Gln
<220> FEATURE:
<221> NAME/KEY: MOD_RES
<222> LOCATION: (211)..(212)
<223> OTHER INFORMATION: Any amino acid except Asp
<220> FEATURE:
<221> NAME/KEY: MOD_RES
<222> LOCATION: (242)..(243)
<223> OTHER INFORMATION: Any amino acid except Gln
<220> FEATURE:
<221> NAME/KEY: MOD_RES
<222> LOCATION: (269)..(270)
<223> OTHER INFORMATION: Any amino acid except Asp

<400> SEQUENCE: 44

Ala Gln His Asp Glu Ala Xaa Xaa Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
```

```
            50                  55                  60
Asn Lys Asp Xaa Xaa Ser Ala Phe Tyr Glu Ile Leu Asn Met Pro Asn
 65                  70                  75                  80

Leu Asn Glu Ala Gln Arg Asn Gly Phe Ile Gln Ser Leu Lys Xaa Xaa
                 85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Xaa Xaa Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Xaa Xaa Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Xaa Xaa Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Xaa Xaa Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Xaa Xaa Asn Ala Phe Tyr Glu Ile Leu His Leu Pro Asn Leu Thr
                245                 250                 255

Glu Glu Gln Arg Asn Gly Phe Ile Gln Ser Leu Lys Xaa Xaa Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 45
<211> LENGTH: 291
<212> TYPE: PRT
<213> ORGANISM: Staphylococcus aureus

<400> SEQUENCE: 45

Ala Gln His Asp Glu Ala Lys Lys Asn Ala Phe Tyr Gln Val Leu Asn
 1               5                  10                  15

Met Pro Asn Leu Asn Ala Asp Gln Arg Asn Gly Phe Ile Gln Ser Leu
                20                  25                  30

Lys Ala Ala Pro Ser Gln Ser Ala Asn Val Leu Gly Glu Ala Gln Lys
            35                  40                  45

Leu Asn Asp Ser Gln Ala Pro Lys Ala Asp Ala Gln Gln Asn Asn Phe
        50                  55                  60

Asn Lys Asp Lys Lys Ser Ala Phe Tyr Glu Ile Leu Asn Met Pro Asn
 65                  70                  75                  80

Leu Asn Glu Ala Gln Arg Asn Gly Phe Ile Gln Ser Leu Lys Ala Ala
                 85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125
```

```
Ala Phe Tyr Glu Ile Leu Asn Met Pro Asn Leu Asn Glu Glu Gln Arg
130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
                260                 265                 270

Val Ser Lys Glu Ile Leu Ala Glu Ala Lys Lys Leu Asn Asp Ala Gln
            275                 280                 285

Ala Pro Lys
        290

<210> SEQ ID NO 46
<211> LENGTH: 291
<212> TYPE: PRT
<213> ORGANISM: Staphylococcus aureus
<220> FEATURE:
<221> NAME/KEY: MOD_RES
<222> LOCATION: (60)..(61)
<223> OTHER INFORMATION: Any amino acid except Gln

<400> SEQUENCE: 46

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Xaa Xaa Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
```

```
                    180                 185                 190
His Leu Pro Asn Leu Asn Glu Glu Gln Arg Asn Gly Phe Ile Gln Ser
            195                 200                 205

Leu Lys Ala Ala Pro Ser Gln Ser Ala Asn Leu Leu Ala Glu Ala Lys
            210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
            275                 280                 285

Ala Pro Lys
        290

<210> SEQ ID NO 47
<211> LENGTH: 291
<212> TYPE: PRT
<213> ORGANISM: Staphylococcus aureus

<400> SEQUENCE: 47

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
            115                 120                 125

Ala Phe Tyr Glu Ile Leu Asn Met Pro Asn Leu Asn Glu Glu Gln Arg
        130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
            195                 200                 205

Leu Lys Ala Ala Pro Ser Gln Ser Ala Asn Leu Leu Ala Glu Ala Lys
            210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255
```

```
Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 48
<211> LENGTH: 292
<212> TYPE: PRT
<213> ORGANISM: Staphylococcus aureus

<400> SEQUENCE: 48

Met Ala Gln His Asp Glu Ala Lys Lys Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Ala Ala Pro Ser Gln Ser Ala Asn Val Leu Gly Glu Ala Gln
        35                  40                  45

Lys Leu Asn Asp Ser Gln Ala Pro Lys Ala Asp Ala Lys Arg Asn Asn
    50                  55                  60

Phe Asn Lys Asp Lys Lys Ser Ala Phe Tyr Glu Ile Leu Asn Met Pro
65                  70                  75                  80

Asn Leu Asn Glu Ala Gln Arg Asn Gly Phe Ile Gln Ser Leu Lys Ala
                85                  90                  95

Ala Pro Ser Gln Ser Thr Asn Val Leu Gly Glu Ala Lys Lys Leu Asn
            100                 105                 110

Glu Ser Gln Ala Pro Lys Ala Asp Asn Asn Phe Asn Lys Glu Lys Lys
        115                 120                 125

Asn Ala Phe Tyr Glu Ile Leu Asn Met Pro Asn Leu Asn Glu Glu Gln
    130                 135                 140

Arg Asn Gly Phe Ile Gln Ser Leu Lys Ala Ala Pro Ser Gln Ser Ala
145                 150                 155                 160

Asn Leu Leu Ser Glu Ala Lys Lys Leu Asn Glu Ser Gln Ala Pro Lys
                165                 170                 175

Ala Asp Asn Lys Phe Asn Lys Glu Lys Lys Asn Ala Phe Tyr Glu Ile
            180                 185                 190

Leu His Leu Pro Asn Leu Asn Glu Glu Gln Arg Asn Gly Phe Ile Gln
        195                 200                 205

Ser Leu Lys Ala Ala Pro Ser Gln Ser Ala Asn Leu Leu Ala Glu Ala
    210                 215                 220

Lys Lys Leu Asn Asp Ala Gln Ala Pro Lys Ala Asp Asn Lys Phe Asn
225                 230                 235                 240

Lys Glu Lys Lys Asn Ala Phe Tyr Glu Ile Leu His Leu Pro Asn Leu
                245                 250                 255

Thr Glu Glu Gln Arg Asn Gly Phe Ile Gln Ser Leu Lys Ala Ala Pro
            260                 265                 270

Ser Val Ser Lys Glu Ile Leu Ala Glu Ala Lys Lys Leu Asn Asp Ala
        275                 280                 285

Gln Ala Pro Lys
    290

<210> SEQ ID NO 49
<211> LENGTH: 291
<212> TYPE: PRT
<213> ORGANISM: Staphylococcus aureus
```

```
<220> FEATURE:
<221> NAME/KEY: MOD_RES
<222> LOCATION: (7)..(8)
<223> OTHER INFORMATION: Any amino acid except Gln
<220> FEATURE:
<221> NAME/KEY: MOD_RES
<222> LOCATION: (34)..(35)
<223> OTHER INFORMATION: Any amino acid except Asp
<220> FEATURE:
<221> NAME/KEY: MOD_RES
<222> LOCATION: (60)..(61)
<223> OTHER INFORMATION: Any amino acid except Gln
<220> FEATURE:
<221> NAME/KEY: MOD_RES
<222> LOCATION: (68)..(69)
<223> OTHER INFORMATION: Any amino acid except Gln
<220> FEATURE:
<221> NAME/KEY: MOD_RES
<222> LOCATION: (95)..(96)
<223> OTHER INFORMATION: Any amino acid except Asp
<220> FEATURE:
<221> NAME/KEY: MOD_RES
<222> LOCATION: (126)..(127)
<223> OTHER INFORMATION: Any amino acid except Gln
<220> FEATURE:
<221> NAME/KEY: MOD_RES
<222> LOCATION: (153)..(154)
<223> OTHER INFORMATION: Any amino acid except Asp
<220> FEATURE:
<221> NAME/KEY: MOD_RES
<222> LOCATION: (184)..(185)
<223> OTHER INFORMATION: Any amino acid except Gln
<220> FEATURE:
<221> NAME/KEY: MOD_RES
<222> LOCATION: (211)..(212)
<223> OTHER INFORMATION: Any amino acid except Asp
<220> FEATURE:
<221> NAME/KEY: MOD_RES
<222> LOCATION: (242)..(243)
<223> OTHER INFORMATION: Any amino acid except Gln
<220> FEATURE:
<221> NAME/KEY: MOD_RES
<222> LOCATION: (269)..(270)
<223> OTHER INFORMATION: Any amino acid except Asp

<400> SEQUENCE: 49

Ala Gln His Asp Glu Ala Xaa Xaa Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Xaa Xaa Asn Asn Phe
50                  55                  60

Asn Lys Asp Xaa Xaa Ser Ala Phe Tyr Glu Ile Leu Asn Met Pro Asn
65                  70                  75                  80

Leu Asn Glu Ala Gln Arg Asn Gly Phe Ile Gln Ser Leu Lys Xaa Xaa
            85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Xaa Xaa Asn
        115                 120                 125

Ala Phe Tyr Glu Ile Leu Asn Met Pro Asn Leu Asn Glu Glu Gln Arg
        130                 135                 140

Asn Gly Phe Ile Gln Ser Leu Lys Xaa Xaa Pro Ser Gln Ser Ala Asn
145                 150                 155                 160

Leu Leu Ser Glu Ala Lys Lys Leu Asn Glu Ser Gln Ala Pro Lys Ala
                165                 170                 175
```

```
Asp Asn Lys Phe Asn Lys Glu Xaa Xaa Asn Ala Phe Tyr Glu Ile Leu
                180                 185                 190

His Leu Pro Asn Leu Asn Glu Glu Gln Arg Asn Gly Phe Ile Gln Ser
            195                 200                 205

Leu Lys Xaa Xaa Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Xaa Xaa Asn Ala Phe Tyr Glu Ile Leu His Leu Pro Asn Leu Thr
                245                 250                 255

Glu Glu Gln Arg Asn Gly Phe Ile Gln Ser Leu Lys Xaa Xaa Pro Ser
            260                 265                 270

Val Ser Lys Glu Ile Leu Ala Glu Ala Lys Lys Leu Asn Asp Ala Gln
    275                 280                 285

Ala Pro Lys
    290

<210> SEQ ID NO 50
<211> LENGTH: 67
<212> TYPE: PRT
<213> ORGANISM: Staphylococcus aureus
<220> FEATURE:
<221> NAME/KEY: MOD_RES
<222> LOCATION: (7)..(8)
<223> OTHER INFORMATION: Any amino acid except Gln
<220> FEATURE:
<221> NAME/KEY: MOD_RES
<222> LOCATION: (34)..(35)
<223> OTHER INFORMATION: Any amino acid except Asp
<220> FEATURE:
<221> NAME/KEY: MOD_RES
<222> LOCATION: (60)..(61)
<223> OTHER INFORMATION: Any amino acid except Gln

<400> SEQUENCE: 50

Ala Gln His Asp Glu Ala Xaa Xaa Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Xaa Xaa Asn Asn Phe
    50                  55                  60

Asn Lys Asp
65

<210> SEQ ID NO 51
<211> LENGTH: 67
<212> TYPE: PRT
<213> ORGANISM: Staphylococcus aureus
<220> FEATURE:
<221> NAME/KEY: MOD_RES
<222> LOCATION: (7)..(8)
<223> OTHER INFORMATION: Any amino acid except Gln
<220> FEATURE:
<221> NAME/KEY: MOD_RES
<222> LOCATION: (34)..(35)
<223> OTHER INFORMATION: Any amino acid except Asp

<400> SEQUENCE: 51

Ala Gln His Asp Glu Ala Xaa Xaa Asn Ala Phe Tyr Gln Val Leu Asn
1               5                   10                  15
```

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
 50                  55                  60

Asn Lys Asp
 65

<210> SEQ ID NO 52
<211> LENGTH: 67
<212> TYPE: PRT
<213> ORGANISM: Staphylococcus aureus

<400> SEQUENCE: 52

Ala Gln His Asp Glu Ala Lys Lys Asn Ala Phe Tyr Gln Val Leu Asn
 1               5                  10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
 50                  55                  60

Asn Lys Asp
 65

<210> SEQ ID NO 53
<211> LENGTH: 68
<212> TYPE: PRT
<213> ORGANISM: Staphylococcus aureus

<400> SEQUENCE: 53

Met Ala Gln His Asp Glu Ala Lys Lys Asn Ala Phe Tyr Gln Val Leu
 1               5                  10                  15

Asn Met Pro Asn Leu Asn Ala Asp Gln Arg Asn Gly Phe Ile Gln Ser
            20                  25                  30

Leu Lys Ala Ala Pro Ser Gln Ser Ala Asn Val Leu Gly Glu Ala Gln
        35                  40                  45

Lys Leu Asn Asp Ser Gln Ala Pro Lys Ala Asp Ala Lys Arg Asn Asn
 50                  55                  60

Phe Asn Lys Asp
 65

<210> SEQ ID NO 54
<211> LENGTH: 67
<212> TYPE: PRT
<213> ORGANISM: Staphylococcus aureus

<400> SEQUENCE: 54

Ala Gln His Asp Glu Ala Gln Asn Ala Phe Tyr Gln Val Leu Asn
 1               5                  10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

```
Leu Asn Asp Ser Gln Ala Pro Lys Ala Asp Ala Gln Gln Asn Asn Phe
 50                  55                  60

Asn Lys Asp
 65
```